(12) United States Patent
Maekawa et al.

(10) Patent No.: US 12,240,945 B2
(45) Date of Patent: Mar. 4, 2025

(54) COMPOUND, RESIN, POLYCARBONATE RESIN, AND OPTICAL MOLDED ARTICLE

(71) Applicant: MITSUI CHEMICALS, INC., Tokyo (JP)

(72) Inventors: Shintaro Maekawa, Ichihara (JP); Yoshiyuki Totani, Ichihara (JP); Kosuke Mano, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 18/346,987

(22) Filed: Jul. 5, 2023

(65) Prior Publication Data

US 2023/0348669 A1 Nov. 2, 2023

Related U.S. Application Data

(63) Continuation of application No. 17/779,161, filed as application No. PCT/JP2021/027779 on Jul. 27, 2021, now Pat. No. 11,746,187.

(30) Foreign Application Priority Data

Jul. 28, 2020 (JP) ................... 2020-127221

(51) Int. Cl.
  C07C 33/36 (2006.01)
  C08G 64/16 (2006.01)
  G02B 1/04 (2006.01)

(52) U.S. Cl.
  CPC .......... *C08G 64/1608* (2013.01); *C07C 33/36* (2013.01); *G02B 1/041* (2013.01)

(58) Field of Classification Search
  USPC ....................................................... 528/370
  See application file for complete search history.

(56) References Cited

U.S. PATENT DOCUMENTS

| 2014/0255836 A1 | 9/2014 | Nakata et al. |
| 2014/0255837 A1 | 9/2014 | Nakata et al. |

(Continued)

FOREIGN PATENT DOCUMENTS

| CN | 102649766 A | 8/2012 | | |
| CN | 105801389 A | * 7/2016 | ............. | C07C 45/26 |

(Continued)

OTHER PUBLICATIONS

CN 105801389A Machine Translation (Year: 2016).*
JP 2013010864 Machine Translation (Year: 2013).*

*Primary Examiner* — Terressa Boykin
(74) *Attorney, Agent, or Firm* — BUCHANAN INGERSOLL & ROONEY PC

(57) ABSTRACT

Provided is a compound represented by General Formula (1)

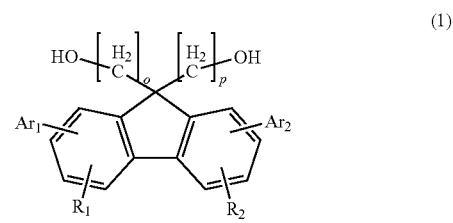

in General Formula (1), $Ar_1$ and $Ar_2$ independently represent a group selected from the following Formulae,

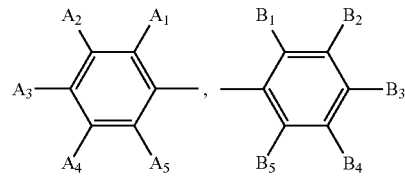

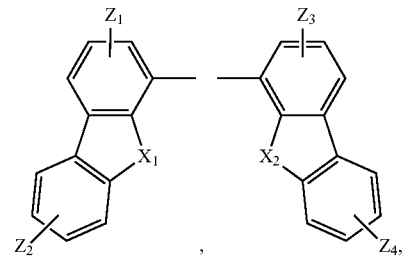

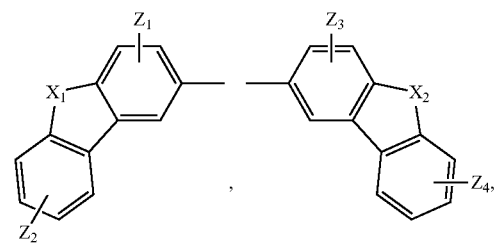

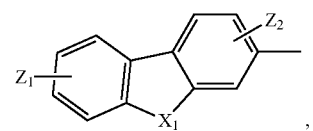

(Continued)

-continued

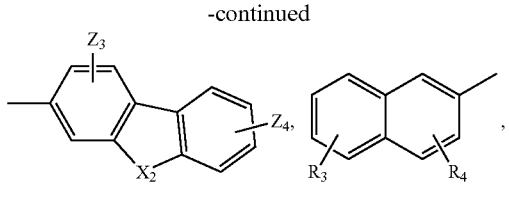
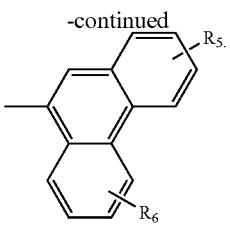

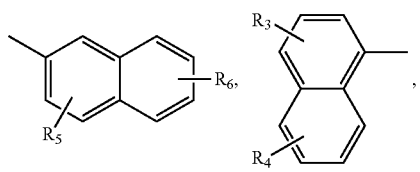

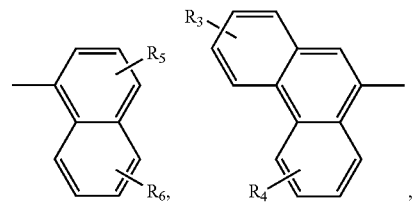

10 Claims, No Drawings

(56) References Cited

U.S. PATENT DOCUMENTS

2021/0147621 A1 5/2021 Yamada et al.
2023/0022186 A1 1/2023 Maekawa et al.

FOREIGN PATENT DOCUMENTS

| | | | |
|---|---|---|---|
| JP | 2005187661 A | | 7/2005 |
| JP | 2005241962 A | | 9/2005 |
| JP | 2008222965 A | | 9/2008 |
| JP | 2013010864 A | * | 1/2013 |
| JP | 2014197173 A | | 10/2014 |
| JP | 2020012094 A | | 1/2020 |
| WO | 2006041190 A1 | | 4/2006 |
| WO | 2010/061896 A1 | | 6/2010 |
| WO | 2021131942 A1 | | 7/2021 |

* cited by examiner

COMPOUND, RESIN, POLYCARBONATE RESIN, AND OPTICAL MOLDED ARTICLE

CROSS-REFERENCE TO RELATED APPLICATIONS

This application is a continuation of U.S. application Ser. No. 17/779,161, filed on May 24, 2022, which is a U.S. national stage application of PCT/JP2021/027779, filed on Jul. 27, 2021, which claims priority to Japanese Patent Application No. 2020-127221, filed on Jul. 28, 2020, the entire contents of all of which are hereby incorporated by reference.

TECHNICAL FIELD

The present invention relates to a compound, a resin obtained from the compound or a polycarbonate resin, and an optical molded article containing the resin or the polycarbonate resin.

BACKGROUND ART

Optical glass or an optical resin is used as a material for an optical lens used in an optical system of various kinds of cameras such as a camera, a film-integrated camera, and a video camera. The optical glass is excellent in heat resistance, transparency, dimensional stability, chemical resistance, and the like, and there are various kinds of materials having various refractive indices and Abbe numbers. However, there are problems that the material cost is high, the molding processability is poor, and the productivity is low.

On the other hand, an optical lens formed of an optical resin has an advantage that mass production can be achieved by injection molding. For example, a polycarbonate resin or the like is used in camera lenses. However, in recent years, there has been a demand for the development of resins having a high refractive index due to lightness, thinness, shortness, and miniaturization of products. In general, since in a case where the refractive index of an optical material is high, lens elements having the same refractive index can be realized with a surface having a smaller curvature, the aberration amount generated on this surface can be reduced. As a result, it is possible to reduce the number of lenses, reduce the eccentricity sensitivity of a lens, and reduce the thickness and weight of a lens.

Examples of techniques related to the optical resin include those described in Patent Documents 1 and 2.

In Patent Document 1 (Japanese Unexamined Patent Publication No. 2005-241962), an optical lens that is formed of a polycarbonate resin having a fluorene structure is described.

In Patent Document 2 (Japanese Unexamined Patent Publication No. 2005-187661), a method for easily improving a refractive index by blending (mixing and adding) a sulfur-containing compound with a fluorene-containing polyester is described.

RELATED DOCUMENT

Patent Documents

[Patent Document 1] Japanese Unexamined Patent Publication No. 2005-241962
[Patent Document 2] Japanese Unexamined Patent Publication No. 2005-187661

SUMMARY OF THE INVENTION

Technical Problem

However, the polycarbonate resin as described in Patent Document 1 has a low refractive index and is not a sufficiently satisfactory resin.

In addition, as described in Patent Document 2, in a case where the sulfur-containing compound is blended with the fluorene-containing polyester, the refractive index is improved. However, in a case where the heat stability is lowered due to the addition of a low molecular weight component, and the compatibility of the two components to be blended is poor, the transparency may decrease.

The present invention has been made in view of the above circumstances, and an object of the present invention is to provide a resin and a polycarbonate resin capable of realizing an optical molded article having a high refractive index and excellent transparency.

Solution to Problem

The present inventors have diligently studied to provide a polycarbonate resin capable of realizing an optical molded article having a high refractive index and excellent transparency. As a result, the present inventors have found that an optical molded article having a high refractive index and excellent transparency can be realized by a resin obtained by polymerization of a compound represented by the following Formula (1), and have reached the present invention.

According to the present invention, a compound represented by the following General Formula (1), a resin obtained from the compound, a polycarbonate resin derived from the compound, and an optical molded article are provided.

[1] A compound represented by General Formula (1),

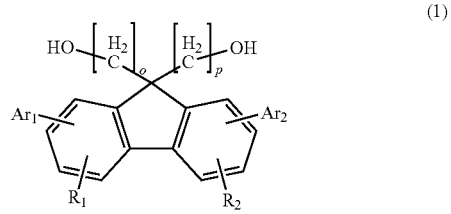

in which in General Formula (1), $Ar_1$ and $Ar_2$ independently represent a group selected from the following Formulae,

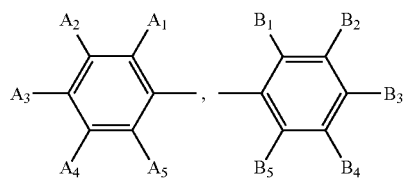

-continued

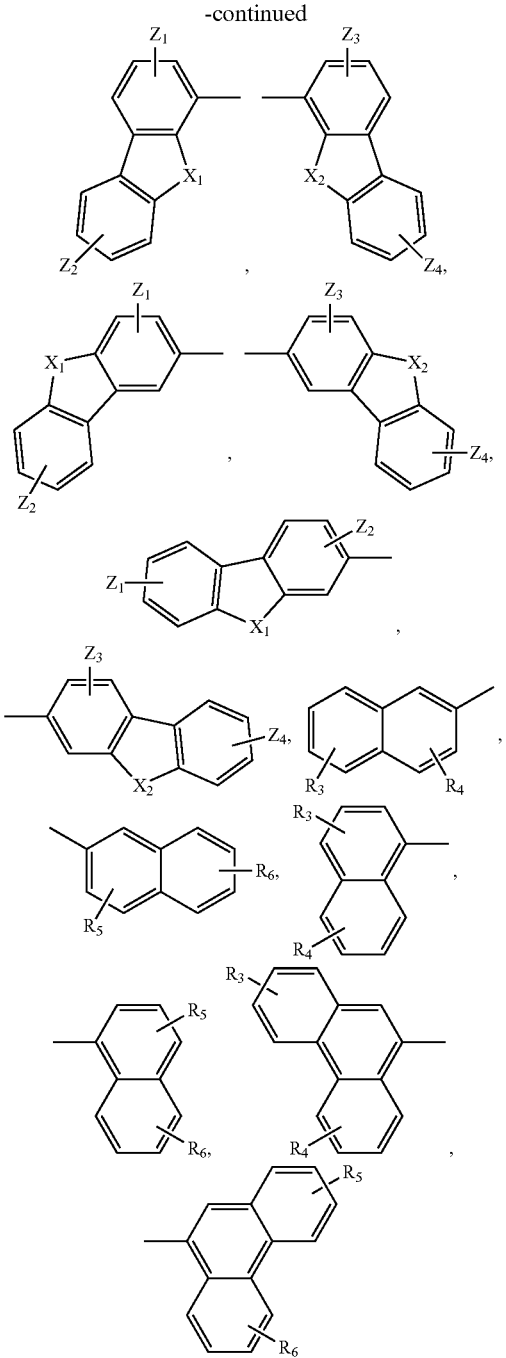

where, $R_1$ to $R_6$ each represent a hydrogen atom, a hydrocarbon group, or a heteroatom-containing hydrocarbon group,
$A_1$ to $A_5$ and $B_1$ to $B_5$ each represent a hydrogen atom, a hydrocarbon group, or a heteroatom-containing hydrocarbon group,
at least one of $A_1$ to $A_5$ is a —$Y_1$—$Ar_3$ group,
at least one of $B_1$ to $B_5$ is a —$Y_2$—$Ar_4$ group,
$Y_1$ and $Y_2$ each represent a single bond or a linking group,
$Ar_3$ and $Ar_4$ each represent an aromatic group,
$X_1$ to $X_4$ each are —O—, —S—, —NR'—, or —C(Me)$_2$-,
$Z_1$ to $Z_4$ each represent a hydrocarbon atom, a hydrocarbon group, or a heteroatom-containing hydrocarbon group, R' represents a hydrogen atom, a hydrocarbon group, or a heteroatom-containing hydrocarbon group, and and p each represent an integer of 1 to 4.

[2] The compound according to [1], in which in General Formula (1), o and p each are 2.

[3] The compound according to [1] or [2], in which in General Formula (1), $Ar_1$ and $Ar_2$ independently represent a group selected from the following formulae,

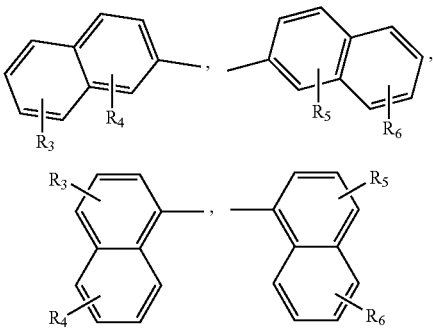

$R_1$ to $R_6$ each represent a hydrogen atom, a hydrocarbon group, or a heteroatom-containing hydrocarbon group, and and p each represent an integer of 1 to 4.

[4] A resin obtained by polymerization of the compound represented by General Formula (1) according to any one of [1] to [3].

[5] A polycarbonate resin derived from the compound represented by General Formula (1) according to any one of [1] to [3].

[6] An optical molded article containing the resin according to [4] or [5].

[7] The optical molded article according to [6], in which the optical molded article is an optical lens.

[8] The optical molded article according to [6], in which the optical molded article is an optical film.

Advantageous Effects of Invention

According to the present invention, it is possible to provide the resin and the polycarbonate resin capable of realizing the optical molded article having the high refractive index and excellent transparency.

DESCRIPTION OF EMBODIMENTS

Hereinafter, embodiments of the present invention will be described. Unless otherwise specified, the term "to" between the numerical values in the text indicates a range of equal to or more than a numerical value and equal to or less than a numerical value.

[Compound]

A compound according to the present embodiment will be described. The compound according to the present embodiment is a compound represented by General Formula (1).

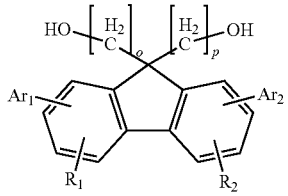

(1)

In General Formula (1), $Ar_1$ and $Ar_2$ independently represent a group selected from the following formulae,

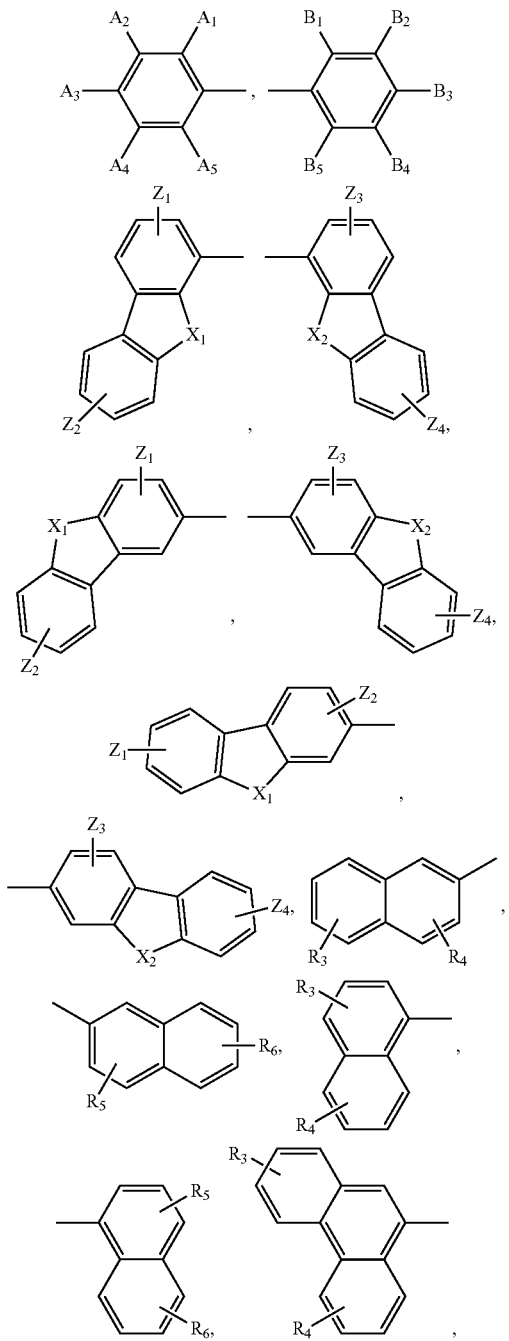

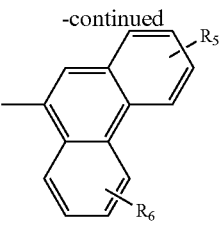

where, $R_1$ to $R_6$ each represent a hydrogen atom, a hydrocarbon group, or a heteroatom-containing hydrocarbon group, $A_1$ to $A_5$ and $B_1$ to $B_5$ each represent a hydrogen atom, a hydrocarbon group, or a heteroatom-containing hydrocarbon group, at least one of $A_1$ to $A_5$ is a —$Y_1$—$Ar_3$ group, at least one of $B_1$ to $B_5$ is a —$Y_2$—$Ar_4$ group, $Y_1$ and $Y_2$ each represent a single bond or a linking group, $Ar_3$ and $Ar_4$ each represent an aromatic group, $X_1$ to $X_4$ each are —O—, —S—, —NR'—, or —C(Me)$_2$-, $Z_1$ to $Z_4$ each represent a hydrogen atom, a hydrocarbon group, or a heteroatom-containing hydrocarbon group, R' represents a hydrogen atom, a hydrocarbon group, or a heteroatom-containing hydrocarbon group, and and p each represent an integer of 1 to 4.

In General Formula (1), $R_1$ to $R_6$ each are preferably independently selected from a hydrogen atom and an alkyl group having 1 to 3 carbon atoms or an aryl group having 6 to 20 carbon atoms, $R_1$ to $R_6$ each are more preferably independently selected from a hydrogen atom, a methyl group, a phenyl group, a biphenyl group, a naphthyl group, and $R_1$ to $R_6$ each are even more preferably a hydrogen atom.

In General Formula (1), o and p each are an integer of 1 to 4, preferably an integer of 1 or 2, and more preferably an integer of 2. By setting o and p to the above range, a polycarbonate resin obtained from the compound of General Formula (1) has excellent heat resistance.

In one embodiment, $Ar_1$ and $Ar_2$ in General Formula (1) independently represent a group selected from the following formulae,

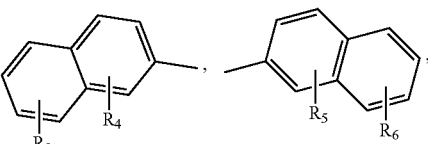

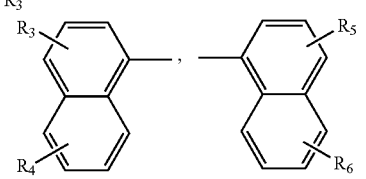

$R_1$ to $R_6$ each represent a hydrogen atom, a hydrocarbon group, or a heteroatom-containing hydrocarbon group, and o and p each represent an integer of 1 to 4.

Examples of preferred aspects of $Ar_1$ and $Ar_2$ in General Formula (1) each include the following formulae.

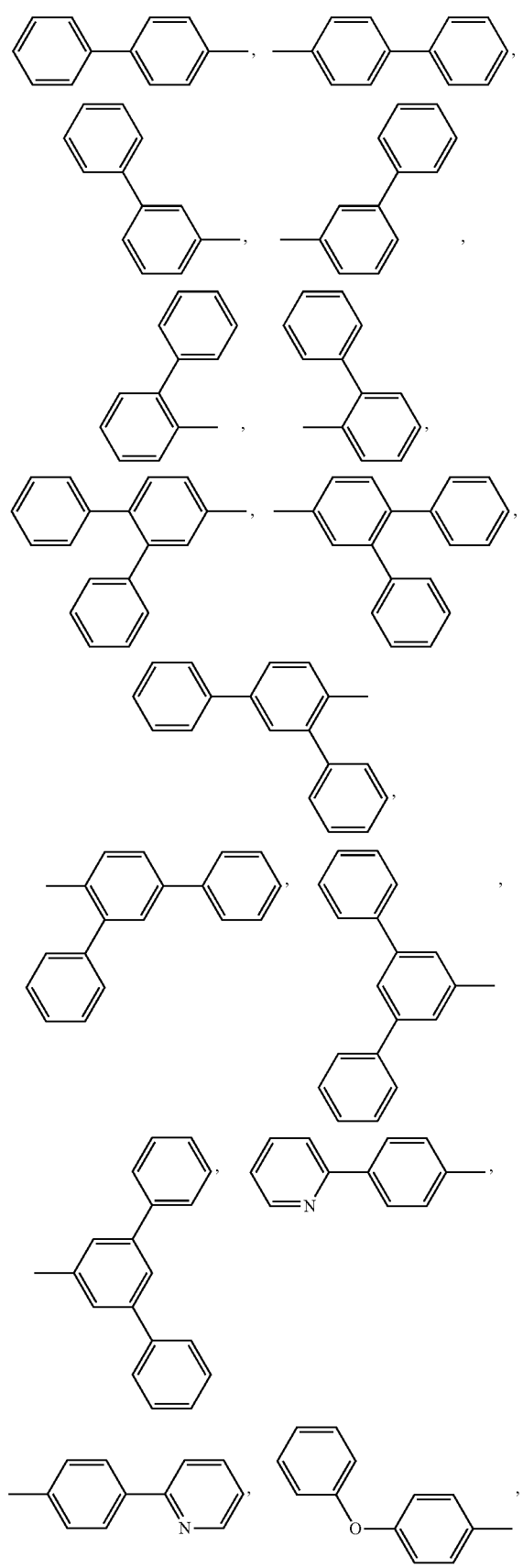
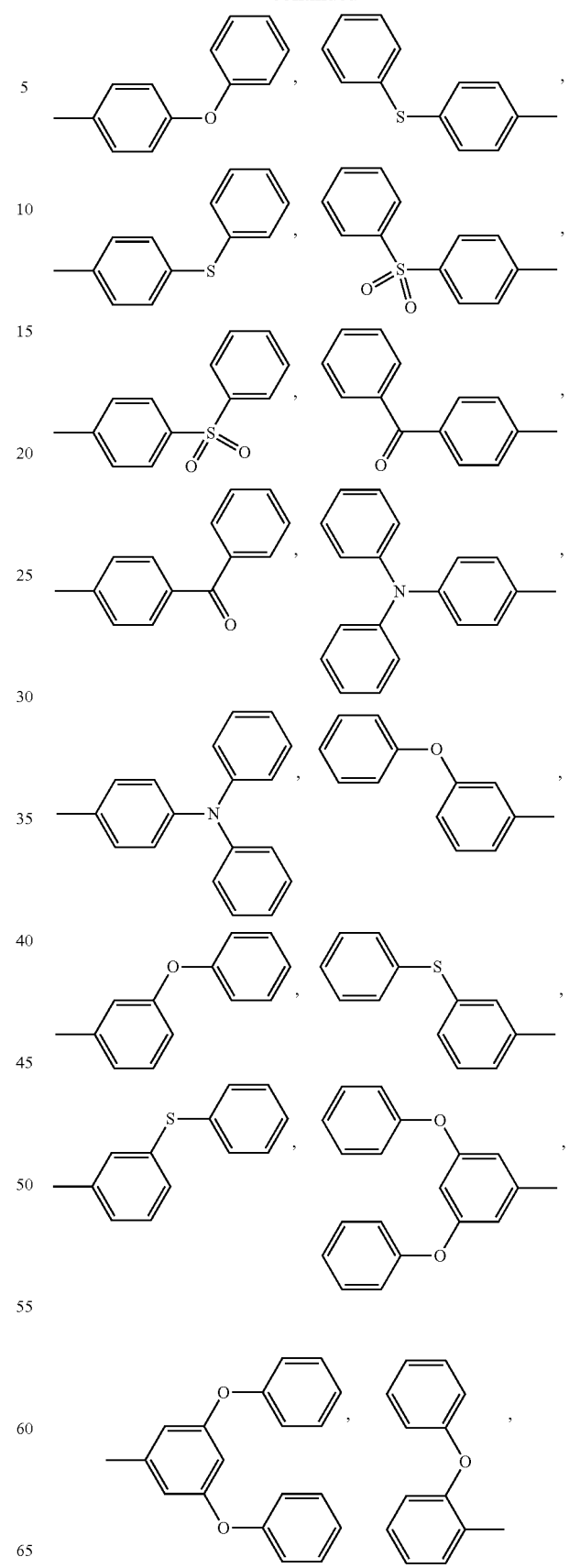

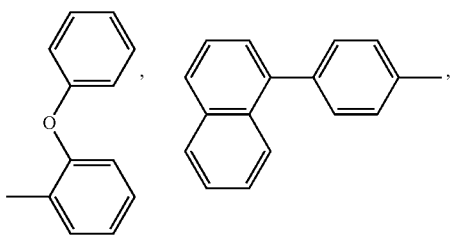

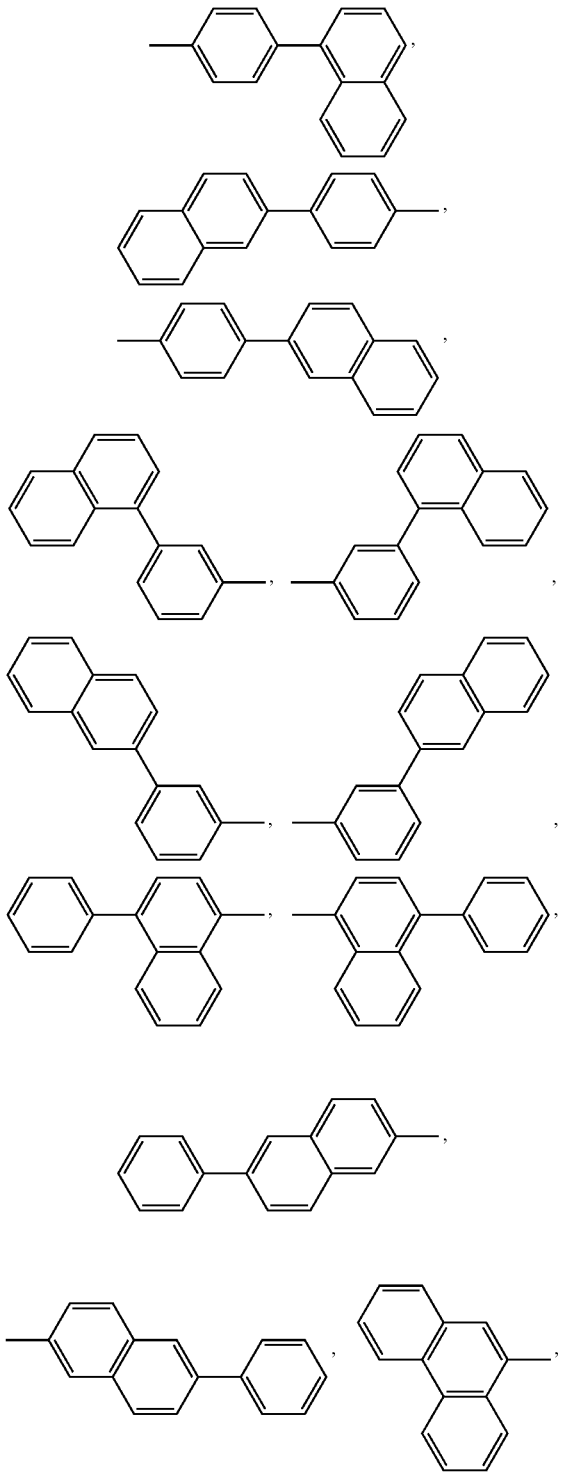

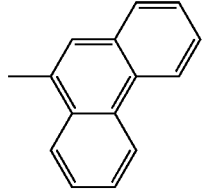

Examples of the compound represented by General Formula (1) include 9,9-bis(1'-hydroxymethyl)-2,7-dinaphthalen-2"-yl-9H-fluorene, 9,9-bis(1'-hydroxymethyl)-2,7-dinaphthalen-1"-yl-9H-fluorene, 9,9-bis(1'-hydroxymethyl)-3,6-dinaphthalen-2"-yl-9H-fluorene, 9,9-bis(1'-hydroxymethyl)-3,6-dinaphthalen-1"-yl-9H-fluorene, 9,9-bis(1'-hydroxymethyl)-2,7-di-p-biphenyl-9H-fluorene, 9,9-bis(1'-hydroxymethyl)-2,7-di-m-biphenyl-9H-fluorene, 9,9-bis(1'-hydroxymethyl)-2,7-bis(3",5"-diphenylphenyl)-9H-fluorene, 9,9-bis(1'-hydroxymethyl)-2,7-bis[dibenzo[b,d]furan-4"-yl]-9H-fluorene, 9,9-bis(1'-hydroxymethyl)-2,7-bis[dibenzo[b,d]thiophen-4"-yl]-9H-fluorene, 9,9-bis(1'-hydroxymethyl)-2,7-bis(4"-phenoxyphenyl)-9H-fluorene, 9,9-bis(1'-hydroxymethyl)-2,7-bis(4"-phenylnaphthalen-1"-yl)-9H-fluorene, 9,9-bis(1'-hydroxymethyl)-2,7-bis[4-(naphthalen-2-yl)phenyl]-9H-fluorene, 9,9-bis(1'-hydroxymethyl)-2,7-bis[3-(naphthalen-2-yl)phenyl]-9H-fluorene, 9,9-bis(2'-hydroxyethyl)-2,7-dinaphthalen-2"-yl-9H-fluorene, 9,9-bis(2'-hydroxyethyl)-2,7-dinaphthalen-1"-yl-9H-fluorene, 9,9-bis(2'-hydroxyethyl)-3,6-dinaphthalen-2"-yl-9H-fluorene, 9,9-bis(2'-hydroxyethyl)-3,6-dinaphthalen-1"-yl-9H-fluorene, 9,9-bis(2'-hydroxyethyl)-2,7-di-p-biphenyl-9H-fluorene, 9,9-bis(2'-hydroxyethyl)-2,7-di-m-biphenyl-9H-fluorene, 9,9-bis(2'-hydroxyethyl)-2,7-di-o-biphenyl-9H-fluorene, 9,9-bis(2'-hydroxyethyl)-2,7-bis(3",5"-diphenylphenyl)-9H-fluorene, 9,9-bis(2'-hydroxyethyl)-2,7-bis[dibenzo[b,d]]furan-4"-yl]-9H-fluorene, 9,9-bis(2'-hydroxyethyl)-2,7-bis[dibenzo[b,d]thiophen-4"-yl]-9H-fluorene, 9,9-bis(2'-hydroxyethyl)-2,7-bis(4"-phenoxyphenyl)-9H-fluorene, 9,9-bis(2'-hydroxyethyl)-2,7-bis(3",5"-diphenoxyphenyl)-9H-fluorene, 9,9-bis(2'-hydroxyethyl)-2,7-bis(4"-phenylnaphthalen-1"-yl)-9H-fluorene, 9,9-bis(2'-hydroxyethyl)-2,7-bis[4-(naphthalen-2-yl)phenyl]-9H-fluorene, 9,9-bis(2'-hydroxyethyl)-2,7-bis[3-(naphthalen-2-yl)phenyl]-9H-fluorene, 9,9-bis(2'-hydroxyethyl)-2,7-bis[3-(naphthalen-1-yl)phenyl]-9H-fluorene, 9,9-bis(2'-hydroxyethyl)-2,7-bis[4-(naphthalen-1-yl)phenyl]-9H-fluorene, 9,9-bis(2'-hydroxyethyl)-2,7-diphenanthryl-9"-yl-9H-fluorene, 9,9-bis(2'-hydroxyethyl)-2,7-bis[9",9"-dimethyl-9"-fluoren-2"-yl]-9H-fluorene, 9,9-bis(3'-hydroxypropyl)-2,7-dinaphthalen-2"-yl-9H-fluorene, 9,9-bis(3'-hydroxypropyl)-2,7-dinaphthalen-1"-yl-9H-fluorene, 9,9-bis(3'-hydroxypropyl)-3,6-dinaphthalen-2"-yl-9H-fluorene, 9,9-bis(3'-hydroxypropyl)-3,6-dinaphthalen-1"-yl-9H-fluorene, 9,9-bis(4'-hydroxybutyl)-2,7-dinaphthalen-2"-yl-9H-fluorene, 9,9-bis(4'-hydroxybutyl)-2,7-dinaphthalen-1"-yl-9H-fluorene, 9,9-bis(4'-hydroxybutyl)-3,6-dinaphthalen-2"-yl-9H-fluorene, 9,9-bis(4'-hydroxybutyl)-3,6-dinaphthalen-1"-yl-9H-fluorene, 9,9-bis(4'-hydroxybutyl)-3,6-bis[4-(naphthalen-2-yl)phenyl]-9H-fluorene, and the like.

Among these, preferred examples thereof can include 9,9-bis(2'-hydroxyethyl)-2,7-dinaphthalen-2"-yl-9H-fluorene, and 9,9-bis(2'-hydroxyethyl)-2,7-dinaphthalen-1"-yl-9H-fluorene. Such a compound may be used alone or two or more compounds may be used in combination.

[Method for Producing Compound Represented by General Formula (1)]

The compound represented by General Formula (1) according to the present embodiment can be synthesized by the following steps (i) and (ii).

Step (i): Dihalogeno-9H-fluorene such as 2,7-dibromo-9H-fluorene or 3,6-dibromo-9H-fluorene is treated with a base (for example, sodium hydroxide, potassium hydroxide, sodium carbonate, potassium carbonate, sodium hydride, potassium hydride, methoxy sodium, ethoxy sodium, t-butoxy sodium, t-butoxy potassium, and n-butyllithium) in a solvent (for example, tetrahydrofuran, 1,4-dioxane, N,N-dimethylformamide, N,N-dimethylacetamide, dimethylsulfoxide, and sulfolane) to extract 9th hydrogen of dihalogeno-9H-fluorene, and thereafter, reacts with hydroxyalkyl having a leaving group (here, examples of a leaving group can include halogen such as chlorine, bromine, iodine, a p-toluenesulfonyloxy group, a methylsulfonyloxy group, a trifluoromethylsulfonyloxy group, and the like) to produce 9,9-bis(hydroxyalkyl)-dihalogeno-9H-fluorene such as 9,9-bis(hydroxyalkyl)-2,7-dibromo-9H-fluorene or 9,9-bis(hydroxyalkyl)-3,6-dibromo-9H-fluorene.

Step (ii): 9,9-bis(hydroxyalkyl)-dihalogeno-9H-fluorene such as 9,9-bis(hydroxyalkyl)-2,7-dibromo-9H-fluorene or 9,9-bis(hydroxyalkyl)-3,6-dibromo-9H-fluorene, which is obtained in Step (i), reacts with naphthyl boric acid in a solvent (for example, toluene and water, tetrahydrofuran and water, and dimethyl sulfoxide and water) in the presence of a base (for example, sodium carbonate, potassium carbonate, sodium acetate, potassium acetate, sodium phosphate, and potassium phosphate) and a palladium-based catalyst such as and tetrakis palladium (triphenylphosphine) to produce the compound represented by General Formula (1) of purpose under a condition of so-called Suzuki-Miyaura Coupling.

Here, the reaction of step (i) can be carried out at any temperature between −78° C. and the boiling point of the solvent. In addition, as reaction conditions, general alkylation reaction conditions can be applied. As desired, a hydroxy group of hydroxyalkyl having a leaving group is protected with any protecting group (for example, an ester group such as an acetyl group), an ether group such as a tetrahydropyranyl group, a carbonic acid ester group such as a t-butoxycarbonyl group, and then may be deprotected at the end.

The reaction of step (ii) can be carried out at any temperature between room temperature and the boiling point of the solvent. As reaction conditions, the reaction conditions generally used in the so-called Suzuki-Miyaura coupling can be applied.

[Resin]

One aspect of the present invention is a resin obtained by polymerization of a compound represented by General Formula (1).

Here, examples of the resin obtained by polymerization of the compound represented by General Formula (1) include a polyester resin, a polyurethane resin, a polycarbonate resin, and a polyether resin.

The polyester resin can be obtained by reacting the compound represented by General Formula (1) with an aromatic dicarboxylic acid (for example, terephthalic acid, isophthalic acid, or 2,6-naphthalenedicarboxylic acid), or an aliphatic dicarboxylic acid (for example, oxalic acid, malonic acid, or succinic acid).

The polyurethane resin can be obtained by reacting the compound represented by General Formula (1) with an aromatic diisocyanate (for example, toluene diisocyanate or xylylene diisocyanate) or an aliphatic diisocyanate (for example, pentamethylene diisocyanate, hexamethylene diisocyanate, or cyclohexanedimethylene diisocyanate).

As will be described later, the polycarbonate resin can be obtained by reacting the compound represented by General Formula (1) with a carbonate precursor such as a carbonic acid diester.

The polyether resin can be obtained by reacting the compound represented by General Formula (1) with an aliphatic dihalogen compound (for example, dibromoethane or dibromopropane) in presence of a base.

In these resins, a reactant other than the compound represented by General Formula (1) of the present application may be used alone or a plurality of reactants may be used in combination. In addition, it is also possible to polymerize a resin by using a dihydroxy compound other than the compound represented by General Formula (1) of the present application, in combination.

In a case where the dihydroxy compound other than the compound represented by General Formula (1) of the present application is used in combination, a ratio of the compound represented by General Formula (1) to the total amount of the compound represented by General Formula (1) of the present application and the dihydroxy compound other than the compound represented by General Formula (1) is preferably equal to or more than 5 mol % and equal to or less than 99 mol %, more preferably equal to or more than 10 mol % and equal to or less than 99 mol %, and even more preferably equal to or more than 15 mol % and equal to or less than 99 mol %.

Here, examples of the dihydroxy compound other than the compound represented by General Formula (1) include bis(4-hydroxyaryl)alkanes such as 9,9-bis[4-(2-hydroxyethoxy)phenyl]fluorene, 9,9-bis[4-(2-hydroxyethoxy)-3-methylphenyl]fluorene, 9,9-bis[4-(2-hydroxyethoxy)-3-ethylphenyl]fluorene, 9,9-bis[4-(2-hydroxyethoxy)-3-n-propylphenyl]fluorene, 9,9-bis[4-(2-hydroxyethoxy)-3-isopropylphenyl]fluorene, 9,9-bis[4-(2-hydroxyethoxy)-3-n-butylphenyl]fluorene, 9,9-bis[4-(2-hydroxyethoxy)-3-sec-butylphenyl]fluorene, 9,9-bis[4-(2-hydroxyethoxy)-3-tert-butylphenyl]fluorene, 9,9-bis[4-(2-hydroxyethoxy)-3-cyclohexylphenyl]fluorene, 9,9-bis[4-(2-hydroxyethoxy)-2-phenylphenyl]fluorene, 9,9-bis[4-(2-hydroxyethoxy)-3-phenylphenyl]fluorene, 9,9-bis[4-(2-hydroxyethoxy)-3-(3-methylphenyl)phenyl]fluorene, bis[4-(2'-hydroxyethoxy)phenyl]sulfide, bis[4-(2'-hydroxyethoxy)-3-methylphenyl]sulfide, bis[4-(2'-hydroxyethoxy)phenyl]sulfone, bis[4-(2'-hydroxyethoxy)-3-methylphenyl]sulfone, bis[4-(2'-hydroxyethoxy)phenyl]sulfoxide, bis(4-hydroxyphenyl)methane, 2,2-bis(4-hydroxyphenyl)propane, 1,1-bis(4-hydroxyphenyl)ethane, 1,1-bis(4-hydroxyphenyl)phenylethane, 2,2-bis(4-hydroxy-3-methylphenyl)propane, 2,2-bis(4-hydroxyphenyl)heptane, 2,2-bis(4-hydroxy-3,5-dichlorophenyl)propane, 2,2-bis(4-hydroxy-3,5-dibromophenyl)propane, and 4,4-dihydroxyphenyl-1,1-m-diisopropylbenzene; bis(hydroxyaryl)cycloalkanes such as 1,1-bis(4-hydroxyphenyl)cyclopentane, 1,1-bis(4-hydroxyphenyl)cyclohexane, 1,1-bis(4-hydroxyphenyl)-3,3,5-trimethylcyclohexane, and 2,2,2,2-tetrahydro-3,3,3,3-tetramethyl-1,1-spirobis[1H inden]-6,6-diol; dihydroxyaryl ethers such as bis(4-hydroxyphenyl)ether, and bis(4-hydroxy-3,5-dichlorophenyl)ether; 9,9-bis(4-hydroxyphenyl)fluorene, 9,9-bis(4-hydroxy-3-methylphenyl)fluorene, 9,9-bis(4-hydroxy-3-tert-butylphenyl)fluorene, 9,9-bis(4-hydroxy-3-isopropylphenyl)fluorene, 9,9-bis(4-hydroxy-3-cyclohexylphenyl)fluorene, and 9,9-bis(4-hydroxy-3-phenylphenyl)fluorene; ethylene glycol, 1,3-propanediol, 1,4-butanediol, 1,5-pentanediol, 1,6-hexanediol, 1,4-cyclohexanedimethanol, 2,2-dimethyl-1,3-propanediol, 1,10-decanediol, diethylene glycol, tetraethylene glycol, norbornane dimethanol, decahydronaphthalenedimethanol, tricyclo[5.2.1.0$^{2,6}$]decandimethanol, pentacyclopentadecanedimethanol, cyclopentane-1,3-dimethanol, spiroglycol, and the like.

[Polycarbonate Resin]

The polycarbonate resin according to the present embodiment is produced by using the compound represented by General Formula (1) according to the present embodiment. The polycarbonate resin according to the present embodiment has a structural unit represented by Formula (1p) and derived from the compound represented by General Formula (1). Such a polycarbonate resin can realize an optical molded article having a high refractive index and excellent transparency. As a result, the polycarbonate resin can be suitably used as a material for an optical lens.

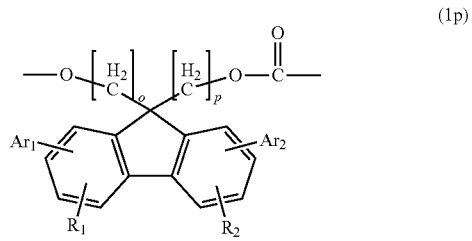

(1p)

In Formula (1p), $Ar_1$ and $Ar_2$, $R_1$ and $R_2$, and o and p each are synonymous with those in Formula (1). The same applies to the preferred aspects.

A preferred weight average molecular weight in terms of polystyrene (Mw) of the polycarbonate resin according to the present embodiment is preferably equal to or greater than $1.5 \times 10^3$ and equal to or smaller than $2.0 \times 10^3$, and more preferably equal to or greater than $2.0 \times 10^3$ and equal to or smaller than $1.2 \times 10^5$.

In a case where Mw is equal to or greater than the above lower limit value, it is preferable that the obtained molded article can be suppressed from being fragile. In a case where Mw is equal to or smaller than the above upper limit value, the melt viscosity becomes more appropriate, so that the resin can be easily taken out after production, fluidity further becomes better, and injection molding becomes easier in a molten state, which are preferable.

A refractive index (n633) of the polycarbonate resin according to the present embodiment at 23° C. and a wavelength of 633 nm is preferably equal to or greater than 1.70 and equal to or smaller than 1.85, more preferably equal to or greater than 1.70 and equal to or smaller than 1.82, even more preferably equal to or greater than 1.71 and equal to or smaller than 1.81, and particularly preferably equal to or greater than 1.72 and equal to or smaller than 1.81.

The polycarbonate resin according to the present embodiment can be blended with another resin and used for producing a molded article. Examples of other resins include polyamide, polyacetal, polycarbonate, modified polyphenylene ether, polyethylene terephthalate, polybutylene terephthalate, and the like.

Furthermore, an antioxidant, a mold release agent, an ultraviolet absorber, a fluidity modifier, a crystal nucleating agent, a strengthening agent, a dye, an antistatic agent, an antibacterial agent, and the like can be added to the polycarbonate resin according to the present embodiment.

Examples of a molding method include compression molding, casting, roll processing, extrusion molding, stretching, and the like, in addition to injection molding, but the molding method is not limited thereto.

In a case where the polycarbonate resin according to the present embodiment is used for injection molding, the glass transition temperature (Tg) is preferably equal to or higher than 80° C. and equal to or lower than 190° C., more preferably equal to or higher than 85° C. and equal to or lower than 180° C., and even more preferably equal to or higher than 90° C. and equal to or lower than 170° C. In a case where Tg is equal to or higher than the above lower limit value, a range of temperature in use is wider, which is preferable. In a case where Tg is equal to or lower than the above upper limit value, the melting temperature of the resin decreases, and decomposition and coloring of the resin are less likely to occur, which is preferable. In addition, in a case where Tg is equal to or lower than the above upper limit value, the difference between the mold temperature and the resin glass transition temperature can be reduced even with a general-purpose mold temperature controller. Therefore, it is easy to use and preferable in applications in which strict surface accuracy is required for a product.

The optical molded article obtained by using the polycarbonate resin according to the present embodiment preferably has a total transmittance of equal to or greater than 82%, more preferably has a total transmittance of equal to or greater than 85%, in which each total transmittance is measured in accordance with JIS K-7361-1 (1997), and is by no means inferior to a bisphenol A-type polycarbonate resin and the like.

[Method for Producing Polycarbonate Resin]

The polycarbonate resin according to the embodiment can be produced by using the compound represented by General Formula (1) as a raw material. Specifically, the compound represented by General Formula (1) reacts with a carbonate precursor such as a carbonic acid diester by a melt polycondensation method, in presence of a basic compound catalyst, a transesterification catalyst, or a mixed catalyst constituted of both, or in absence of a catalyst, to produce the polycarbonate resin.

Examples of the carbonic acid diester used to produce the polycarbonate resin according to the present embodiment include diphenyl carbonate, di-p-tolyl carbonate, di-m-tolyl carbonate, di-o-tolyl carbonate, bis(p-chlorophenyl)carbonate, bis(m-chlorophenyl)carbonate, bis(o-chlorophenyl)carbonate, m-cresyl carbonate, dimethyl carbonate, diethyl carbonate, di-n-butyl carbonate, dicyclohexyl carbonate, and the like. Among these, diphenyl carbonate is preferred. Diphenyl carbonate is preferably used in a ratio of 0.97 to 1.20 mol and more preferably used in a ratio of 0.98 to 1.10 mol, with respect to 1 mol of the compound represented by General Formula (1).

Examples of the basic compound catalyst used in the production of the polycarbonate resin according to the present embodiment include alkali metal compounds, alkaline earth metal compounds, nitrogen-containing compounds, and the like. As such compounds, organic acid salts, inorganic salts, oxides, hydroxides, hydrides or alkoxides, or quaternary ammonium hydroxides and salts thereof, amines of alkali metals, alkaline earth metal compounds, or the like are preferably used, and these compounds can be used alone or in combination.

Examples of the alkali metal compounds include organic acid salts, inorganic salts, oxides, hydroxides, hydrides, alkoxides, and the like of alkali metals. Specific examples thereof for use include sodium hydroxide, potassium hydroxide, cesium hydroxide, lithium hydroxide, sodium hydrogencarbonate, sodium carbonate, potassium hydrogencarbonate, potassium carbonate, cesium carbonate, lithium carbonate, sodium acetate, potassium acetate, cesium acetate, lithium acetate, sodium stearate, potassium stearate, cesium stearate, lithium stearate, sodium borohydride, sodium borophenylate, sodium benzoate, potassium benzoate, cesium benzoate, lithium benzoate, disodium hydrogenphosphate, dipotassium hydrogenphosphate, dilithium hydrogenphosphate, disodium phenylphosphate, a disodium salt, a dipotassium salt, a dicesium salt, or a dilithium salt of bisphenol A, a sodium salt, a potassium salt, a cesium salt, or a lithium salt of phenol, and the like.

Examples of the alkaline earth metal compounds include organic acid salts, inorganic salts, oxides, hydroxides, hydrides, alkoxides, or the like of alkaline earth metal compounds. Specific examples thereof for use include magnesium hydroxide, calcium hydroxide, strontium hydroxide, barium hydroxide, magnesium hydrogencarbonate, calcium hydrogencarbonate, strontium hydrogencarbonate, barium hydrogencarbonate, magnesium carbonate, calcium carbonate, strontium carbonate, barium carbonate, magnesium acetate, calcium acetate, strontium acetate, barium acetate, magnesium stearate, calcium stearate, calcium benzoate, magnesium phenylphosphate, and the like.

Examples of the nitrogen-containing compounds include quaternary ammonium hydroxides and salts thereof, amines, and the like. Specific examples thereof for use include quaternary ammonium hydroxides having an alkyl group such as tetramethylammonium hydroxide, tetraethylammonium hydroxide, tetra n-propylammonium hydroxide, tetra n-butylammonium hydroxide, trimethylbenzylammonium hydroxide, or an aryl group; tertiary amines such as triethylamine, dimethylbenzylamine, triphenylamine; secondary amines such as diethylamine and dibutylamine; primary amines such as n-propylamine and n-butylamine; imidazoles such as 2-methylimidazole, 2-phenylimidazole, and benzoimidazole; or bases such as ammonia, tetramethylammonium borohydride, tetra n-butylammonium borohydride, tetra n-butylammonium tetraphenylborate, tetraphenylammonium tetraphenylborate, or basic salts, and the like.

As the transesterification catalyst, salts such as zinc, tin, zirconium, lead, and the like are preferably used, and these salts can be used alone or in combination. Specific examples of the transesterification catalyst for use include zinc acetate, zinc benzoate, zinc 2-ethylhexanoate, tin chloride (II), tin chloride (IV), tin acetate (II), tin acetate (IV), dibutyltin dilaurate, dibutyltin oxide, dibutyltin dimethoxide, zirconium acetylacetonate, zirconium oxyacetate, zirconium tetrabutoxide, lead acetate (II), lead acetate (IV), and the like.

Each of these catalysts is used at a ratio of $10^{-9}$ to $10^{-3}$ mol, preferably $10^{-7}$ to $10^{-4}$ mol, with respect to a total of 1 mol of the compound represented by General Formula (1).

The melt polycondensation method is a method of performing melt polycondensation using the above described raw material and catalyst under heating and normal pressure or reduced pressure while removing by-products through a transesterification reaction.

In the melt polycondensation method according to the present embodiment, the reaction is desirably carried out in a state in which the compound represented by General Formula (1) and the carbonic acid diester are melted in a reaction vessel, and the reaction is then carried out in a state where by-product monohydroxy compounds are kept in the reaction vessel.

In order to keep the by-product monohydroxy compounds, a reacting apparatus can be closed, or can be vacuumed or pressurized for pressure control purposes The reaction time required for this step is preferably equal to or more than 20 minutes and equal to or less than 240 minutes, more preferably equal to or more than 40 minutes and equal to or less than 180 minutes, and particularly preferably equal to or more than 60 minutes and equal to or less than 150 minutes. During this step, in a case where the by-product monohydroxy compounds are distilled off immediately upon the generation of the by-product monohydroxy compounds, the finally obtained polycarbonate resin is low in the content of high molecular weight components. However, in a case where the by-product monohydroxy compounds are kept in the reaction vessel for a certain period of time, the finally obtained polycarbonate resin is high in the content of high molecular weight components.

In general, a melt polycondensation reaction is carried out in a multi-stage step of two or more stages. Specifically, a first-stage reaction is preferably carried out at a temperature of 120° C. to 260° C., and more preferably carried out at a temperature of 180° C. to 240° C., and preferably carried out under normal pressure or pressure for 0.1 to 5 hours, and more preferably carried out under pressure for 0.5 to 3 hours. Next, the compound represented by General Formula (1) reacts with carbonic acid diester with a reaction temperature being increased while increasing the degree of decompression of the reaction system, and finally, the polycondensation reaction is preferably carried out with the degree of decompression of equal to or lower than 133 Pa (1 mmHg) at a temperature of 200° C. to 350° C. for 0.05 to 2 hours.

The melt polycondensation reaction may be carried out either in a continuous manner or in a batch manner.

The reacting apparatus for use in this reaction may be a vertical reactor equipped with an anchor-type impeller, a Maxblend impeller, a helical ribbon-type impeller or the like, may be a horizontal reactor equipped with a paddle impeller, a grid impeller, a spectacle impeller or the like, or may be an extruder-type reacting apparatus equipped with a screw. In addition, it is suitable to use a reacting apparatus constituted of these reactors in combination as appropriate, in consideration of the viscosity of the polymerized product.

In the polycarbonate resin according to the present embodiment, after the polycondensation reaction is completed, the catalyst may be removed or deactivated in order to maintain heat stability and hydrolysis stability. In general, known methods for catalyst deactivation which involve addition of an acidic substance can suitably be carried out. Specific examples of an acidic substance suitable for use include esters such as butyl benzoate; aromatic sulfonic acids such as p-toluenesulfonic acid; aromatic sulfonic acid esters such as butyl p-toluenesulfonate and hexyl p-toluenesulfonate; phosphoric acids such as phosphorous acid, phosphoric acid and phosphonic acid; phosphorous acid esters such as triphenyl phosphite, monophenyl phosphite, diphenyl phosphite, diethyl phosphite, n-propyl phosphite, n-butyl phosphite, n-hexyl phosphite, n-octyl phosphite, and mono n-octyl phosphite; phosphoric acid esters such as triphenyl phosphate, diphenyl phosphate, monophenyl phosphate, n-butyl phosphate, n-octyl phosphate, and mono n-octyl phosphate; phosphonic acids such as diphenylphosphonic acid, di n-octylphosphonic acid, and di n-butylphosphonic acid; phosphonic acid esters such as diethyl phenylphosphonate; phosphines such as triphenyl phosphine and bis(diphenylphosphino)ethane; boric acids such as boric acid and phenylboric acid; aromatic sulfonates such as n-dodecylbenzenesulfonic acid tetra n-butylphosphonium salt; organic halides such as stearic acid chloride, benzoyl chloride, and p-toluenesulfonic acid chloride; alkyl sulfates such as dimethyl sulfate; organic halides such as benzyl chloride, and the like. Each of these deactivating agents is preferably used in a content of 0.01 to 50 times by mole and more preferably 0.3 to 20 times by mole with respect to the amount of the catalyst. In a case where the content of the deactivating agent is less than 0.01 times by mole with respect to the amount of the catalyst, the deactivating effect is insufficient, which is not preferable. In addition, in a case where the content of the deactivating agent is more than 50 times by mole with respect to the amount of the catalyst, the heat resistance of the resin is lowered, and the molded article is easily colored, which is not preferable.

After the catalyst is deactivated, a step of devolatilizing and removing compounds having the low boiling point in the polymer at a pressure of 13 to 133 Pa (0.1 to 1 mmHg) and a temperature of 200° C. to 350° C. may be provided. In this step, a horizontal evaporator equipped with an impeller that is excellent in surface renewal ability, such as a paddle impeller, a grid impeller, and a spectacle impeller, or a thin film evaporator is suitable for use.

The polycarbonate resin according to the present embodiment is desired to be extremely low in the content of contaminants, which is suitably accomplished by filtration of molten raw materials, filtration of the catalyst solution, and the like. The mesh size of a filter is preferably equal to or smaller than 5 µm, and more preferably equal to or smaller than 1 µm. Furthermore, the generated resin is suitably filtered through a polymer filter. The mesh size of the polymer filter is preferably equal to or smaller than 100 µm, and more preferably equal to or smaller than 30 µm. In addition, a step of collecting resin pellets is, naturally, preferably performed in a low dust environment, and more preferably with cleanness of equal to or less than class 1000.

[Optical Molded Article]

An optical molded article according to the present embodiment contains the polycarbonate resin according to the present embodiment, and the optical molded article can be produced by using the polycarbonate resin according to the present embodiment.

For example, the optical molded article is molded by any method such as an injection molding method, a compression molding method, an injection compression molding method, an extrusion molding method, or a solution casting method.

Since the polycarbonate resin according to the present embodiment is excellent in moldability and heat resistance, the polycarbonate resin can be used particularly advantageously in optical lenses that are required to be produced by injection molding. During the molding, the polycarbonate resin according to the present embodiment can be mixed with other resins such as other polycarbonate resins and polyester resins, and used.

In addition, it is possible to use various types of additives in order to impart various characteristics in a range that does not impair the object of the present embodiment. Examples of additives include antioxidants, processing stabilizers, mold release agents, ultraviolet absorbers, bluing agents, polymeric metal deactivators, flame retardants, lubricants, antistatic agents, heat ray shielding agents, fluorescent dyes (including fluorescent whitening agents), pigments, light scattering agents, reinforcing fillers, surfactants, antibacterial agents, plasticizers, compatibilizers, other resins, elastomers, and the like.

Examples of antioxidants include triethylene glycol-bis[3-(3-tert-butyl-5-methyl-4-hydroxyphenyl)propionate], 1,6-hexanediol-bis[3-(3,5-di-tert-butyl-4-hydroxyphenyl) propionate], pentaerythritol-tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzyl)benzene, N,N-hexamethylene bis(3,5-di-tert-butyl-4-hydroxy-hydrocinnamide), 3,5-di-tert-butyl-4-hydroxy-benzyl phosphonate-diethyl ester, tris(3,5-di-tert-butyl-4-hydroxybenzyl) isocyanurate, and 3,9-bis{1,1-dimethyl-2-[β-(3-tert-butyl-4-hydroxy-5-methylphenyl)propionyloxy]ethyl}-2,4,8,10-tetraoxaspiro(5,5)undecane, and the like.

The content of the antioxidant in the polycarbonate resin is preferably 0.001 to 0.3 parts by mass with respect to 100 parts by mass of the polycarbonate resin.

Examples of processing stabilizers include phosphorus-based processing heat stabilizers, sulfur-based processing heat stabilizers, and the like.

Examples of phosphorus-based processing heat stabilizers include phosphorous acid, phosphoric acid, phosphonous acid, phosphonic acid, esters thereof, and the like. Specific examples thereof include triphenyl phosphite, tris(nonylphenyl) phosphite, tris(2,4-di-tert-butylphenyl) phosphite, tris(2,6-di-tert-butylphenyl) phosphite, tri n-decyl phosphite, tri n-octyl phosphite, tri n-octadecyl phosphite, di n-decyl monophenyl phosphite, di n-octyl monophenyl phosphite, diisopropyl monophenyl phosphite, mono n-butyl diphenyl phosphite, monodecyl diphenyl phosphite, mono n-octyl diphenyl phosphite, bis(2,6-di-tert-butyl-4-methylphenyl) pentaerythritol diphosphite, 2,2-methylene bis(4,6-di-tert-butylphenyl) octyl phosphite, bis(n-nonylphenyl) pentaerythritol diphosphite, bis(2,4-dicumylphenyl) pentaerythritol diphosphite, bis(2,4-di-tert-butylphenyl) pentaerythritol diphosphite, distearyl pentaerythritol diphosphite, tri n-butyl phosphate, triethyl phosphate, trimethyl phosphate, triphenyl phosphate, diphenyl monoorthoxenyl phosphate, di n-butyl phosphate, di n-octyl phosphate, diisopropyl phosphate, dimethyl benzenephosphonate, diethyl benzenephosphonate, dipropyl benzenephosphonate, tetrakis(2,4-di-t-butylphenyl)-4,4'-biphenylenediphosphonite, tetrakis(2,4-di-t-butylphenyl)-4,3'-biphenylenediphosphonite, tetrakis(2,4-di-t-butylphenyl)-3,3'-biphenylenediphosphonite, bis(2,4-di-tert-butylphenyl)-4-phenyl-phenylphosphonite and bis(2,4-di-tert-butylphenyl)-3-phenyl-phenylphosphonite, and the like.

The content of the phosphorus-based processing heat stabilizer in the polycarbonate resin is preferably 0.001 to 0.2 parts by mass with respect to 100 parts by mass of the polycarbonate resin.

Examples of sulfur-based processing heat stabilizers include pentaerythritol-tetrakis(3-laurylthiopropionate), pentaerythritol-tetrakis(3-myristylhiopropionate), pentaerythritol-tetrakis(3-stearylthiopropionate), dilauryl-3,3'-thiodipropionate, dimyristyl-3,3'-thiodipropionate, distearyl-3,3'-thiodipropionate, and the like.

The content of the sulfur-based processing heat stabilizer in the polycarbonate resin is preferably 0.001 to 0.2 parts by mass with respect to 100 parts by mass of the polycarbonate resin.

As a mold release agent, a mold release agent of which equal to or more than 90% by mass is formed of esters of alcohols and fatty acids is preferable. Specific examples of the esters of alcohols and fatty acids include esters of monohydric alcohol and fatty acid and partial esters or whole esters of polyhydric alcohol and fatty acid. As the ester of a monohydric alcohol and a fatty acid, an ester of a monohydric alcohol having 1 to 20 carbon atoms and a saturated fatty acid having 10 to 30 carbon atoms is preferable. In addition, as the partial ester or whole ester of a polyhydric alcohol and a fatty acid, a partial ester or whole ester of polyhydric alcohol having 1 to 25 carbon atoms and saturated fatty acid having 10 to 30 carbon atoms is preferable.

Examples of esters of a monohydric alcohol and a saturated fatty acid include stearyl stearate, palmityl palmitate, n-butyl stearate, methyl laurate, isopropyl palmitate, and the like. Examples of partial esters or whole esters of polyhydric alcohols and saturated fatty acids include whole esters or partial esters of dipentaerythritol such as stearic acid monoglyceride, stearic acid diglyceride, stearic acid triglyceride, stearic acid monosorbitate, behenic acid monoglyceride, capric acid monoglyceride, lauric acid monoglyceride, pentaerythritol monostearate, pentaerythritol tetrastearate, pentaerythritol tetrapelargonate, propylene glycol monostearate, biphenyl biphenate, sorbitan monostearate, 2-ethylhexyl stearate, and dipentaerythritol hexastearate.

The content of these mold release agents is preferably in a range of 0.005 to 2.0 parts by mass with respect to 100 parts by mass of the polycarbonate resin, more preferably in a range of 0.01 to 0.6 parts by mass, and even more preferably in a range of 0.02 to 0.5 parts by mass.

As the ultraviolet absorber, it is possible to include at least one type of ultraviolet absorber selected from the group consisting of a benzotriazole-based ultraviolet absorber, a benzophenone-based ultraviolet absorber, a triazine-based ultraviolet absorber, a cyclic imino ester-based ultraviolet absorber, and a cyanoacrylate-based ultraviolet absorber. The ultraviolet absorbers listed below may be used alone or in a combination of two or more types.

Examples of benzotriazole-based ultraviolet absorbers include 2-(2-hydroxy-5-methylphenyl) benzotriazole, 2-(2-hydroxy-5-tert-octylphenyl) benzotriazole, 2-(2-hydroxy-3,5-dicumylphenyl) phenylbenzotriazole, 2-(2-hydroxy-3-tert-butyl-5-methylphenyl)-5-chlorobenzotriazole, 2,2'-methylenebis[4-(1,1,3,3-tetramethylbutyl)-6-(2N-benzotriazol-2-yl) phenol], 2-(2-hydroxy-3,5-di-tert-butylphenyl) benzotriazole, 2-(2-hydroxy-3,5-di-tert-butylphenyl)-5-chlorobenzotriazole, 2-(2-hydroxy-3,5-di-tert-amylphenyl) benzotriazole, 2-(2-hydroxy-5-tert-octylphenyl) benzotriazole, 2-(2-hydroxy-5-tert-butylphenyl) benzotriazole, 2-(2-hydroxy-4-n-octyloxyphenyl) benzotriazole, 2,2'-methylenebis(4-cumyl-6-benzotriazolephenyl), 2,2'-p-phenylenebis(1,3-benzoxazin-4-one), 2-[2-hydroxy-3-(3,4,5,6-tetrahydrophthalimidomethyl)-5-methylphenyl] benzotriazole, and the like.

Examples of benzophenone-based ultraviolet absorbers include 2,4-dihydroxybenzophenone, 2-hydroxy-4-methoxybenzophenone, 2-hydroxy-4-n-octyloxybenzophenone, 2-hydroxy-4-benzyloxybenzophenone, 2-hydroxy-4-methoxy-5-sulfoxybenzophenone, 2-hydroxy-4-methoxy-5-sulfoxytrihydratebenzophenone, 2,2'-dihydroxy-4-methoxybenzophenone, 2,2',4,4'-tetrahydroxybenzophenone, 2,2'-dihydroxy-4,4'-dimethoxybenzophenone, 2,2'-dihydroxy-4,4'-dimethoxy-5-sodium sulfoxybenzophenone, bis(5-benzoyl-4-hydroxy-2-methoxyphenyl) methane, 2-hydroxy-4-n-dodecyloxybenzophenone, 2-hydroxy-4-methoxy-2'-carboxybenzophenone, and the like.

Examples of triazine ultraviolet absorbers include 2-(4,6-diphenyl-1,3,5-triazin-2-yl)-5-[(n-hexyl)oxy]-phenol, 2-(4,6-bis(2,4-dimethylphenyl)-1,3,5-triazin-2-yl)-5-[(n-octyl) oxy]-phenol, and the like.

Examples of cyclic imino ester-based ultraviolet absorbers include 2,2'-bis(3,1-benzoxazin-4-one), 2,2'-p-phenylenebis(3,1-benzoxazine-4-one), 2,2'-m-phenylenebis(3,1-benzoxazin-4-one), 2,2'-(4,4'-diphenylene)bis(3,1-benzoxazin-4-one), 2,2'-(2,6-naphthalene)bis(3,1-benzoxazin-4-one), 2,2'-(1,5-naphthalene)bis(3,1-benzoxazine-4-one), 2,2'-(2-methyl-p-phenylene)bis(3,1-benzoxazin-4-one), 2,2'-(2-nitro-p-phenylene)bis(3,1-benzoxazin-4-one) and 2,2'-(2-chloro-p-phenylene)bis(3,1-benzoxazin-4-one), and the like.

Examples of cyanoacrylate-based ultraviolet absorbers include 1,3-bis-[(2'-cyano-3',3'-diphenylacryloyl)oxy]-2,2-bis[[(2-cyano-3,3-diphenylacryloyl)oxy]methyl]propane, and 1,3-bis-[(2-cyano-3,3-diphenylacryloyl)oxy]benzene, and the like.

The content of the ultraviolet absorber is preferably 0.01 to 3.0 parts by mass with respect to 100 parts by mass of the polycarbonate resin, and more preferably 0.02 to 1.0 part by mass, and even more preferably 0.05 to 0.8 parts by mass. With this blending amount range, it is possible to impart sufficient weather resistance to a polycarbonate resin according to the application thereof.

Examples of bluing agents include Macrolex Violet B and Macrolex Blue RR made by Bayer, and Polysynthren Blue RLS made by Clariant, and the like.

The bluing agent is effective to eliminate the yellowness of the polycarbonate resin. In particular, in a case of a polycarbonate resin to which weather resistance is imparted, a certain amount of ultraviolet absorber is blended, thus, the polycarbonate resin molded article tends to be slightly yellow due to the "action and color of the ultraviolet absorber" and blending a bluing agent therein is particularly effective for imparting natural transparency to a sheet or lens.

The blending amount of the bluing agent is, for example, preferably 0.05 to 1.5 ppm with respect to the polycarbonate resin, and more preferably 0.1 to 1.2 ppm.

The polycarbonate resin according to the present embodiment exhibits a high refractive index and excellent heat resistance, and has a fluidity suitable for molding. Furthermore, since optical distortion is unlikely to occur due to a low degree of birefringence, the optical molded article can be advantageously used, as an optical molded article, not only for optical lenses, but also as an electrically conductive transparent substrate for use in liquid crystal displays, organic EL displays, solar photovoltaic cells, and the like, and suitable for use as a structural material or functional material for optical components such as optical disks, liquid crystal panels, optical cards, sheets, films, optical fibers, connectors, evaporated plastic reflecting mirrors, displays, and the like.

A surface of such an optical molded article may be provided with a coating layer such as an antireflection layer or a hard coat layer, as necessary. Such an antireflection layer may be constituted of a single layer or multiple layers, and may be formed of an organic material or an inorganic material, but is preferably formed of an inorganic material. Specific examples include oxides or fluorides such as silicon oxide, aluminum oxide, zirconium oxide, titanium oxide, cerium oxide, magnesium oxide, magnesium fluoride, and the like.

(Optical Lens)

An optical lens produced by using the polycarbonate resin according to the present embodiment is very useful since the optical lens has a high refractive index and are excellent in heat resistance, and thus can be used in the fields of telescopes, binoculars, television projectors, and others where expensive high refractive index glass lenses have been used in the related art. The optical lens is preferably used in the form of an aspherical lens, as necessary. In the case of the aspherical lens, a single lens achieves substantially zero spherical aberration, which eliminates the need to remove spherical aberration by combining a plurality of spherical lenses, so that light weight and production cost savings can be achieved. Therefore, an aspherical lens is particularly useful as a camera lens among optical lenses.

The optical lens according to the present embodiment is molded by any method such as an injection molding method, a compression molding method, or an injection compression molding method. According to the present embodiment, an aspherical lens with a high refractive index and a low degree of birefringence can be obtained in a simpler manner, which is technically difficult to process in the case of using glass lenses.

(Optical Film)

An optical film produced by using the polycarbonate resin according to the present embodiment is excellent in transparency and heat resistance, and is therefore suitable for use in films for liquid crystal substrates, optical memory cards, and the like.

As described above, the embodiments of the present invention have been described, but these are examples of the present invention, and various configurations other than the above can be adopted.

EXAMPLES

Hereinafter, the present embodiment will be described in detail with reference to Examples and Comparative Examples. The present embodiment is not limited to the description of these examples.

1. Measurement and Evaluation Method

In the following Examples and Comparative Examples, the measurement and evaluation of each physical property were performed by the following method.

1) Weight average molecular weight (Mw) in terms of polystyrene: Gel permeation chromatography (GPC, manufactured by Waters Corporation, 1515, 2414, and 2489) was used to prepare a calibration curve from polystyrene standards of known molecular weight (molecular weight distribution=1) by using chloroform as an eluate. Based on this calibration curve, Mw was calculated from the retention time in GPC.

2) Refractive index (n633): a silicon wafer was coated with a chloroform solution of a resin having a concentration of 8.5 wt % by using a spin coater at 200 rpm for 20 seconds and 1000 rpm for 5 seconds, and baked at 120° C. for 5 minutes and 200° C. for 2 minutes to adjust a sample, and a refractive index and a thickness of a film were calculated by fitting the following optical model to optical measurement data at a wavelength of 200 to 1000 nm by using a spectroscopic ellipsometer GES5E (manufactured by Semilab Semiconductor Physics Laboratory Co., Ltd.).

(Optical Model)

Laminated structure: Film/$SiO_2$ (thickness of 2 nm)/Si substrate (thickness of 500 μm)

Dispersion type of film: Cauchy+Lorentz oscillator model

3) Glass transition temperature (Tg): Measurement is carried out by a differential scanning calorimetry (DSC: DSC-60 manufactured by Shimadzu Corporation).

1. Preparation of Compound Represented by Formula (1)

Example 1

Synthesis of 9,9-bis(2'-hydroxyethyl)-2,7-dinaphthalen-2"-yl-9H-fluorene

Step (i): Synthesis of 9,9-bis(2'-hydroxyethyl)-2,7-dibromo-9H-fluorene

A 500 ml flask was charged with 66.5 g (0.2 mol) of 2,7-dibromo-9H-fluorene, 56 g (0.998 mol) of potassium hydroxide (powder), 3.4 g (0.02 mol) of potassium iodide, 150 ml of dimethyl sulfoxide, and cooled to 10° C. with ice water. Thereafter, 58.4 g (0.467 mol) of 2-bromoethanol was added dropwise over 45 minutes, and the mixture was then stirred overnight at room temperature. Thereafter, the reaction solution was heated to 50° C. and heated and stirred for 40 hours. The reaction mixture was discharged into 2 liters of distilled water and pH was adjusted to 6 with concentrated hydrochloric acid. The obtained solid was filtered and separated, and washed with 3 liters of water. The obtained solid was dissolved in 1 liter of ethyl acetate, washed with 500 ml of distilled water, and concentrated with an evaporator, and chloroform was added to obtain 34.8 g of 9,9-bis(2'-hydroxyethyl)-2,7-dibromo-9H-fluorene as colorless crystals.

Step (ii): Preparation of 9,9-bis(2'-hydroxyethyl)-2,7-dinaphthalen-2"-yl-9H-fluorene A 1-liter flask was charged with 20.75 g (50 mmol) of 9,9-bis(2'-hydroxyethyl)-2,7-dibromo-9H-fluorene, 19.17 g (0.11 mol) of naphthalene-2-boronic acid, 15.3 g (0.11 mol) of potassium carbonate, 250 g of distilled water, and 400 g of dimethyl sulfoxide. 3.0 g of tetrakis(triphenylphosphine) palladium was added to this reaction mixture, the mixture was heated to 100° C., and heated and stirred for 5 hours. After cooling, the produced solid was filtered and separated, washed with 500 g of water, and vacuum dried at 50° C. After drying, the solid was suspended and washed with chloroform to obtain 20.87 g of 9,9-bis(2'-hydroxyethyl)-2,7-dinaphthalen-2"-yl-9H-fluorene as colorless crystals. The melting point measured by DSC was 236° C.

Example 2

Synthesis of 9,9-bis(2'-hydroxyethyl)-2,7-dinaphthalen-2"-yl-9H-fluorene

Step (i): Synthesis of 2-(2'-bromoethoxy)tetrahydropyran

A 2-liter round bottomed flask equipped with a stirrer, a thermometer and a dropping funnel was charged with 150 g (1.20 mol) of 2-bromoethanol and 800 ml of dichloromethane, and cooled with ice water. Thereafter, when the internal temperature reached 5° C., 130 g (1.56 mol) of 3,4-dihydro-2H-pyran was added dropwise at equal to or lower than 10° C. After completion of the dropwise addition, 30 g (0.12 mol) of pyridinium p-toluenesulfonate was added, and the mixture was stirred overnight at room temperature. Thereafter, saturated water of sodium hydrogencarbonate was added, and a dichloromethane layer was washed with water. The obtained dichloromethane layer was concentrated by an evaporator to obtain 255 g of 2-(2'-bromoethoxy)tetrahydropyran as a pale yellow oil.

Step (ii): Synthesis of 9,9-bis[2-(2'-tetrahydropyranyloxy)ethyl]-2,7-dibromo-9H-fluorene A 2-liter round bottomed flask equipped with a stirrer, a thermometer and a reflux tube was charged with 255 g of 2-(2'-bromoethoxy)tetrahydropyran, 270 ml of toluene, and 164 g (0.506 mol) of 2,7-dibromo-9H-fluorene, and 270 ml of an aqueous solution of 50% sodium hydroxide were added thereto. Thereafter, 8.5 g (26.2 mmol) of tetrabutylammonium bromide was added, the mixture was heated to 100° C., and the mixture was heated and stirred for 11.5 hours. Thereafter, the reaction mixture was cooled to room temperature, an aqueous layer was separated, 700 ml of ethyl acetate and 700 ml of distilled water were then added, and the mixture was washed with water. After the washing with water was repeatedly carried out, a layer formed of ethyl acetate and toluene was separated and concentrated by an evaporator. A small amount of seed crystals of 9,9-bis[2-(2'-tetrahydropyranyloxy)ethyl]-2,7-dibromo-9H-fluorene was added to a viscous liquid obtained after concentration, and methanol was added to carry out crystallization. The obtained crystals was filtered, washed with a small amount of methanol, and then recrystallized by heating from 500 ml of methanol to obtain 246 g of 9,9-bis[2-(2'-tetrahydropyranyl) ethoxy]-2,7-dibromo-9H-fluorene of purpose was obtained as pale yellow crystals.

m. p. 98.5° C.

$^1$H-NMR (CDCl3) δ 1.30-1.53 (m, 12H) 2.34-2.38 (t, 4H) 2.70-3.5 (m, 8H) 4.1 (t, 2H), 7.43-7.55 (m, 6H)

Step (iii): Synthesis of 9,9-bis[2-(2'-tetrahydropyranyloxy)ethyl]-2,7-dinaphthalen-2"-yl-9H-fluorene A 1-liter round bottomed flask equipped with a stirrer, a thermometer and a reflux tube was charged with 72.55 g (125 mmol) of 9,9-bis[2-(2'-tetrahydropyranyloxy)ethyl]-2,7-dibromo-9H-fluorene, 475 ml of toluene, 61 g (442 mmol) of potassium carbonate, 47.29 g (275 mmol) of 2-naphthalene boronic acid, and 211 ml of distilled water, and 1.4 g of tetrakis(triphenylphosphine)palladium were added to this reaction mixture while being stirred, and then the resultant mixture was heated up to 80° C. The mixture was heated and stirred at 80° C. for 12 hours, and then cooled to room temperature. After separating the aqueous layer, a toluene layer was washed with distilled water, and then the toluene layer was concentrated by an evaporator. 730 ml of methanol was added to the concentrated residue, and the resultant solid was filtered and separated, and washed with methanol. Thereafter, purification was carried out by silica gel column chromatography (eluent toluene to toluene/ethyl acetate=9/1), and then recrystallization from methyl cellosolve was carried out to obtain 121.01 g of a desired product. Yield 72%, HPLC purity 99.3%, m. p. 148° C., $^1$H-NMR (CDCl$_3$) 51.20-1.70 (m, 12H), 2, 55 (t, 4H), 2.8-3.5 (m, 8H), 4.16 (m, 2H), 7.40-7.65 (m, 4H), 7.70-8.05 (m, 14H), 8.1 (s, 2H)

Step (iv): Synthesis of 9,9-bis(2'-hydroxyethyl)-2,7-dinaphthalen-2"-yl-9H-fluorene A 1-liter round bottomed flask equipped with a stirrer, a thermometer and a reflux tube was charged with 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid, the temperature was increased to 115° C. with stirring, and the mixture was heated and stirred at the same temperature for 4 hours. Thereafter, the mixture was cooled to room temperature, 180 ml of water was added, and the resulting crystals were filtered and separated. The obtained crystals were washed with distilled water, dried under reduced pressure at 50° C., and then suspended and washed with hot methyl cellosolve to obtain 38.73 g of a desired product. Yield 85%, m. p. 249.5° C., $^1$H-NMR (DMSO-d$_6$) δ2.43 (t, 4H), 2.80 (t, 4H), 4.16 (t, 2H), 7.50-7.60 (m, 4H), 7.8-8.1 (m, 12H), 8.35 (s, 2H)

Example 3

Synthesis of 9,9-bis(2'-hydroxyethyl)-2,7-bis[dibenzo[b,d]furan-4"-yl]-9H-fluorene 66.05 g of 9,9-bis[2-(2'-tetrahydropyranyloxy)ethyl]-2,7-bis[dibenzo[b,d]furan-4"-yl]-9H-fluorene was obtained according to the operations described in the step (iii) of Example 2, except that 58.85 g (275 mmol) of dibenzo[b,d]furan-4-yl boronic acid was used instead of using 47.29 g (275 mmol) of 2-naphthalene boronic acid in the step (iii) of Example 2. Yield 70%, HPLC purity 97.5%, m. p. 176.7° C., $^1$H-NMR (CDCl$_3$) δ 1.29-1.45 (10H, m), 1.58 (2H, m), 2.58 (4H, t), 2.98 (2H, q), 3.24 (2H, dt), 3.40 (2H, q), 3.55 (2H, dt), 4.23 (2H, s), 7.39 (2H, t), 7.48 (4H, q), 7.64 (2H, d), 7.68-7.71 (2H, m), 7.90-8.03 (10H, m)

41.03 g of a desired product was obtained according to the operations described in the step (iv) of Example 2, except that 60.00 g (79.4 mmol) of 9,9-bis[2-(2'-tetrahydropyranyloxy)ethyl]-2,7-bis[dibenzo[b,d]furan-4"-yl]-9H-fluorene, 540 ml of methyl cellosolve, 22 ml of distilled water, and 6.2 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 88%, HPLC purity 99.4%, m. p. 247.4° C., $^1$H-NMR (DMSO-d$_6$) δ2.40 (4H, t), 2.98 (4H, m), 4.24 (2H, t), 7.46 (2H, t), 7.58 (4H, dt), 7.82 (4H, dd), 8.03-8.10 (6H, m), 8.22 (4H, dd)

Example 4

Synthesis of 9,9-bis(2'-hydroxyethyl)-2,7-bis[4-(naphthalen-2-yl-)phenyl]-9H-fluorene 68.23 g of 9,9-bis[2-(2'-tetrahydropyranyloxy)ethyl]-2,7-bis[4-(naphthalen-2-yl-)phenyl]-9H-fluorene was obtained according to the operations described in the step (iii) of Example 2, except that 68.22 g (275 mmol) of 4-(naphthalen-2-yl)phenyl boronic acid was used instead of using 47.29 g (275 mmol) of 2-naphthalene boronic acid in the step (iii) of Example 2. Yield 66%, HPLC purity 99.2%, m. p. 209.4° C., $^1$H-NMR (CDCl$_3$) δ 1.26-1.61 (12H, m), 2.55 (4H, t), 2.86 (2H, q), 3.22-3.32 (4H, m), 3.51-3.56 (2H, m), 4.17 (2H, t), 7.49-7.55 (4H, m), 7.67 (2H, d), 7.75 (2H, d), 7.78-7.82 (6H, m), 7.84-7.90 (8H, m), 7.95 (4H, t), 8.13 (2H, s)

41.10 g of a desired product was obtained according to the operations described in the step (iv) of Example 2, except that 60.00 g of 9,9-bis[2-(2'-tetrahydropyranyloxy)ethyl]-2,7-bis[4-(naphthalen-2-yl-)phenyl]-9H-fluorene, 500 ml of methyl cellosolve, 20 ml of distilled water, and 6 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 86%, HPLC purity 99.6%, m. p. 341.3° C., 1H-NMR (DMSO-d$_6$) δ2.41 (4H, t), 2.83 (4H, q), 4.20 (2H, t), 7.53-7.60 (4H, m), 7.83 (2H, d), 7.94-8.00 (16H, m), 8.06 (4H, d), 8.33 (2H, s)

Example 5

Synthesis of 9,9-bis(2'-hydroxyethyl)-2,7-bis[3-(naphthalen-2-yl-)phenyl]-9H-fluorene 70.30 g of 9,9-bis[2-(2'-tetrahydropyranyloxy)ethyl]-2,7-bis[3-(naphthalen-2-yl-)phenyl]-9H-fluorene was obtained according to the operations described in the step (iii) of Example 2, except that 68.22 g (275 mmol) of 3-(naphthalen-2-yl)phenyl boronic acid was used instead of using 47.29 g (275 mmol) of 2-naphthalene boronic acid in the step (iii) of Example 2. Yield 68%, HPLC purity 98.9%, m. p. 171.6° C., $^1$H-NMR (CDCl$_3$) 51.26-1.58 (12H, m), 2.54 (4H, t), 2.86 (2H, q), 3.22-3.30 (4H, m), 3.49-3.54 (2H, m), 4.16 (2H, t), 7.51-7.61 (6H, m), 7.66-7.74 (8H, m), 7.81 (2H, d), 7.84 (2H, dd), 7.90 (2H, d), 7.94-7.99 (6H, m), 8.14 (2H, s)

41.58 g of a desired product was obtained according to the operations described in the step (iv) of Example 2, except that 60.00 g (72.5 mmol) of 9,9-bis[2-(2'-tetrahydropyranyloxy)ethyl]-2,7-bis[3-(naphthalen-2-yl-)phenyl]-9H-fluorene, 500 ml of methyl cellosolve, 20 ml of distilled water, and 5.7 g of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 87%. The final product was purified by column chromatography (eluent: ethyl acetate/chloroform=⅛→¼). HPLC purity 99.7%, m. p. 143.1° C., $^1$H-NMR (DMSO-d$_6$) δ: 2.52 (4H, t), 3.17 (4H, q), 7.51-7.54 (4H, m), 7.60 (2H, t), 7.67-7.69 (2H, m), 7.74 (2H, dd), 7.76 (2H, s), 7.82-7.91 (6H, m), 7.94-7.99 (6H, m), 8.14 (2H, s)

Example 6

Synthesis of 9,9-bis(2'-hydroxyethyl)-2,7-diphenanthren-9"-yl-9H-fluorene 73.62 g of 9,9-bis[2-(2'-tetrahydropyranyloxy)ethyl]-2,7-diphenanthrene 9"-yl-9H-fluorene was obtained according to the operations described in the step (iii) of Example 2, except that 61.06 g (275 mmol) of phenanthren-9-yl boronic acid was used instead of using 47.29 g (275 mmol) of 2-naphthalene boronic acid in the step (iii) of Example 2. Yield 76%, HPLC purity 95.9%, viscous solid, $^1$H-NMR (CDCl$_3$) 51.36-1.64 (12H, m), 2.50 (4H, t), 2.99 (2H, q), 3.30-3.43 (4H, m), 3.58 (2H, dt), 4.29 (2H, s), 7.57 (4H, d), 7.63-7.72 (8H, m), 7.77 (2H, s), 7.90 (2H, d), 7.93-7.95 (2H, m), 8.03 (2H, d), 8.79 (4H, dd)

48.22 g of a desired product was obtained according to the operations described in the step (iv) of Example 2, except that 70.00 g (90.3 mmol) of 9,9-bis[2-(2'-tetrahydropyranyloxy)ethyl]-2,7-diphenanthren-9"-yl-9H-fluorene, 610 ml of methyl cellosolve, 25 ml of distilled water, and 7 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 88%. The final product was purified by column chromatography (eluent: ethyl acetate/chloroform=⅙→¼). HPLC purity 99.3%, m. p. 226.9° C., $^1$H-NMR (DMSO-d$_6$) δ2.48 (4H, t), 3.31 (4H, q), 7.57-7.73 (12H, m), 7.77 (2H, s), 7.95 (6H, dd), 8.79 (4H, dd)

Example 7

Synthesis of 9,9-bis(2'-hydroxyethyl)-2,7-bis[dibenzo[b,d]thiophen-4"-yl]-9H-fluorene 68.87 g of 9,9-bis[2-(2'-tetrahydropyranyloxy)ethyl]-2,7-bis[dibenzo[b,d]thiophen-4"-yl]-9H-fluorene was obtained according to the operations described in the step (iii) of Example 2, except that 62.72 g (275 mmol) of dibenzo[b,d]thiophen-4-yl boronic acid was used instead of using 47.29 g (275 mmol) of 2-naphthalene boronic acid in the step (iii) of Example 2. Yield 70%, HPLC purity 99.1%, viscous solid, $^1$H-NMR (CDCl$_3$) δ 1.28-1.43 (10H, m), 1.55 (2H, m), 2.56 (4H, t), 2.95 (2H, q), 3.22 (2H, dt), 3.37 (2H, q), 3.52 (2H, dt), 4.20 (2H, s), 7.51 (2H, t), 7.68 (4H, q), 7.85 (2H, d), 7.82-7.89 (2H, m), 8.11-8.24 (10H, m)

40.10 g of a desired product was obtained according to the operations described in the step (iv) of Example 2, except that 60.00 g (76.4 mmol) of 9,9-bis[2-(2'-tetrahydropyranyloxy)ethyl]-2,7-bis[dibenzo[b,d]thiophen-4"-yl]-9H-fluorene, 500 ml of methyl cellosolve, 20 ml of distilled water, and 6.0 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 85%, HPLC purity 98.9%, m. p. 223.6° C., $^1$H-NMR (DMSO-d$_6$) δ2.38 (4H, t), 2.93 (4H, dt), 4.26 (2H, t), 7.57 (4H, dd), 7.69-7.71 (4H, m), 7.79 (2H, d), 7.97 (2H, s), 8.04 (2H, dd), 8.10 (2H, d), 8.43-8.47 (4H, dd)

Example 8

Synthesis of 9,9-bis(2'-hydroxyethyl)-2,7-bis[4"-phenoxyphenyl]-9H-fluorene 68.31 g of 9,9-bis[2-(2'-tetrahydropyranyloxy)ethyl]-2,7-bis[4-phenoxyphenyl]-9H-fluorene was obtained according to the operations described in the step (iii) of Example 2, except that 58.86 g (275 mmol) of 4-phenoxyphenyl boronic acid was used instead of using 47.29 g (275 mmol) of 2-naphthalene boronic acid in the step (iii) of Example 2. Yield 72%, HPLC purity 98.8%, viscous solid, $^1$H-NMR (CDCl$_3$) 51.24-1.59 (12H, m), 2.48 (4H, t), 2.81 (2H, q), 3.20-3.27 (4H, m), 3.48-3.54 (2H, m), 4.14 (2H, t), 7.07-7.15 (10H, m), 7.37 (4H, dt), 7.55 (2H, d), 7.60-7.63 (6H, m), 7.74 (2H, d)

38.29 g of a desired product was obtained according to the operations described in the step (iv) of Example 2, except that 60.00 g (79.1 mmol) of 9,9-bis[2-(2'-tetrahydropyranyloxy)ethyl]-2,7-bis[4"-phenoxyphenyl]-9H-fluorene, 530 ml of methyl cellosolve, 22 ml of distilled water, and 6.2 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 82%, HPLC purity 99.7%, m. p. 134.1° C., $^1$H-NMR (DMSO-d$_6$) δ2.34 (4H, t), 2.76 (4H, q), 4.14 (2H, t), 7.07-7.20 (10H, m), 7.43 (4H, t), 7.67 (2H, dd), 7.81 (6H, t), 7.90 (2H, d)

Example 9

Synthesis of 9,9-bis(2'-hydroxyethyl)-2,7-bis[4"-phenylnaphthalen-1"-yl]-9H-fluorene 73.4 g of 9,9-bis[2-(2'-tetrahydropyranyloxy)ethyl]-2,7-bis[4"-phenylnaphthalen-1"-yl-]-9H-fluorene was obtained according to the operations described in the step (iii) of Example 2, except that 68.22 g (275 mmol) of 4-phenylnaphthalen-1-yl boronic acid was used instead of using 47.29 g (275 mmol) of 2-naphthalene boronic acid in the step (iii) of Example 2. Yield 71%, HPLC purity 99.8%, m. p. 230.3° C.,
$^1$H-NMR (CDCl$_3$) 51.36-1.61 (12H, m), 2.50 (4H, t), 2.97 (2H, q), 3.30 (2H, dt), 3.38 (2H, q), 3.57 (2H, dt), 4.27 (2H, s), 7.45-7.58 (20H, m), 7.66 (2H, s), 7.89 (2H), d), 7.98-8.00 (2H, m), 8.05-8.10 (2H, m)

47.95 g of a desired product was obtained according to the operations described in the step (iv) of Example 2, except that 70.00 g (84.6 mmol) of 9,9-bis[2-(2'-tetrahydropyranyloxy)ethyl]-2,7-bis[4"-phenylnaphthalen-1"-yl-]-9H-fluorene, 570 ml of methyl cellosolve, 24 ml of distilled water, and 7.0 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 86%, HPLC purity 99.0%, m. p. 271.4° C.,
$^1$H-NMR (DMSO-d$_6$) δ2.34 (4H, t), 2.95 (4H, dt), 4.24 (2H, t), 7.51-7.63 (20H, m), 7.72 (2H, s), 7.90-7.93 (2H, m), 7.99-8.01 (2H, m), 8.08 (2H, d)

Example 10

Synthesis of 9,9-bis(2'-hydroxyethyl)-2,7-bis[9",9"-dimethyl-9"H-fluoren-2"-yl]-9H-fluorene 76.67 g of 9,9-bis[2-(2'-tetrahydropyranyloxy)ethyl]-2,7-bis[9",9"-dimethyl-9"H-fluoren-2"-yl]-9H-fluorene was obtained according to the operations described in the step (iii) of Example 2, except that 65.47 g (275 mmol) of 9,9-dimethyl-9H-fluoren-2-yl boronic acid was used instead of using 47.29 g (275 mmol) of 2-naphthalene boronic acid in the step (iii) of Example 2. Yield 76%, HPLC purity 91.0%, viscous solid,
$^1$H-NMR (CDCl$_3$) 51.25-1.50 (12H, m), 1.58 (12H, s), 2.56 (4H, t), 2.87 (2H, q), 3.23-3.32 (4H, m), 3.51-3.57 (2H, m), 4.16 (2H, t), 7.32-7.39 (4H, m), 7.47 (2H, dd), 7.62-7.67 (4H, m), 7.69-7.72 (4H, m), 7.76-7.82 (6H, m)

48.21 g of a desired product was obtained according to the operations described in the step (iv) of Example 2, except that 70.00 g (89.7 mmol) of 9,9-bis[2-(2'-tetrahydropyranyloxy)ethyl]-2,7-bis[9",9"-dimethyl-9"H-fluoren-2"-yl]-9H-fluorene, 590 ml of methyl cellosolve, 24 ml of distilled water, and 6.8 ml of concentrated hydrochloric acid were used instead of using 60.00 g (88.9 mmol) of 9,9-bis[2-(2'-tetrahydropyranyloxy)ethyl]-2,7-dinaphthalen-2"-yl-9H-fluorene, 600 ml of methyl cellosolve, 25 ml of distilled water, and 7 ml of concentrated hydrochloric acid in the step (iv) of Example 2. Yield 87%, HPLC purity 96.9%, m. p. 272.3° C.,
$^1$H-NMR (DMSO-d$_6$) δ1.55 (12H, s), 2.42 (4H, t), 2.79 (4H, m), 4.18 (2H, t), 7.33-7.40 (4H, m), 7.59 (2H, dd), 7.76-7.79 (4H, m), 7.88 (2H, d), 7.95 (8H, dd)

Example 11

Synthesis of 9,9-bis(2'-hydroxyethyl)-2,7-dinaphthalen-1"yl-9H-fluorene 65.80 g of 9,9-bis[2 (2'-tetrahydropyranyloxy)ethyl]-2,7-dinaphthyl-1"-yl-9H-fluorene was obtained according to the operations described in the step (iii) of Example 2, except that 47.29 g (275 mmol) of 1-naphthalene boronic acid was used instead of using 47.29 g (275 mmol) of 2-naphthalene boronic acid in the step (iii) of Example 2. Yield 78%, HPLC purity 91.0%, viscous solid,
$^1$H-NMR (CDCl$_3$) 51.14-1.46 (m, 12H), 2.47 (t, 4H), 2.9-3.6 (m, 8H), 4.2 (s, 2H), 7.5-8.1 (m, 20H)

35.13 g of a desired product was obtained according to the operations described in the step (iv) of Example 2, except that 60.00 g (88.9 mmol) of 9,9-bis[2-(2'-tetrahydropyranyloxy)ethyl]-2,7-dinaphthalen-1"yl-9H-fluorene was used instead of using 60.00 g (88.9 mmol) of 9,9-bis[2-(2'-tetrahydropyranyloxy)ethyl]-2,7-dinaphthalen-2"-yl-9H-fluorene in the step (iv) of Example 2. Yield 78%, HPLC purity 95.4%, viscous solid,
$^1$H-NMR (DMSO-d$_6$) δ2.3 (t, 4H), 2.9 (t, 4H), 4.2 (2, 2H), 7.5-8.2 (m, 20H)

Comparative Synthesis Example 1

19.9 g of 9,9-bis(2'-hydroxyethyl)-2,7-didiphenyl-9H-fluorene was obtained as colorless crystals according to the operations described in Example 1, except that 13.41 g (0.11 mol) of phenyl boronic acid was used instead of using 19.17 g (0.11 mol) of naphthalene-2-boronic acid in Example 1.

2. Production of Polycarbonate Resin

Example 12

A reactor equipped with a distiller was charged with 20.26 g (40 mmol) of 9,9-bis(2'-hydroxyethyl)-2,7-dinaphthalen-2"-yl-9H-fluorene obtained in Example 1, 8.56 g (40 mmol) of diphenylcarbonate (hereinafter, abbreviated as "DPC" in some cases), and 15 μL (3×10$^{-6}$ mol) of a 0.02 M-sodium hydrogencarbonate aqueous solution, and the mixture reacted at 240° C. and 100 kPa for one hour. Thereafter, the degree of decompression was adjusted to 19 kPa, and the mixture reacted for 20 minutes. Then, the mixture reacted at the same temperature and the same pressure for 70 minutes. Next, the degree of decompression was adjusted to 16 kPa and the mixture reacted for 20 minutes, and the degree of decompression was further adjusted to 13 kPa and the mixture reacted for 20 minutes. Thereafter, when the degree of decompression was reduced to 130 Pa for 40 minutes and reached a predetermined torque through the reaction at the same pressure for 30 minutes, the vacuum was released with nitrogen gas to extract the polycarbonate resin.

A weight average molecular weight (Mw) of the obtained polycarbonate resin was 32300, and a Tg was 135° C.

A refractive index (n633) of this polycarbonate resin was 1.7608.

Comparative Example 2

A polycarbonate resin was obtained according to the operations in Example 12, except that in Example 12, 16.26 g (40 mmol) of 9,9-bis(2'-hydroxyethyl)-2,7-diphenyl-9H-fluorene was used instead of using 20.26 g (40 mmol) of 9,9-bis(2'-hydroxyethyl)-2,7-dinaphthalen-2"-yl-9H-fluorene obtained in Example 1.

A weight average molecular weight (Mw) of the obtained polycarbonate resin was 28300, and a Tg was 112° C.

A refractive index (n633) of this polycarbonate resin was 1.6959.

Example 13

A reactor equipped with a distiller was charged with 20.26 g (40 mmol) of 9,9-bis(2'-hydroxyethyl)-2,7-dinaphthalen-2"-yl-9H-fluorene obtained in Example 2, 8.56 g (40 mmol) of diphenylcarbonate, and 15 µL (3×10$^{-6}$ mol) of a 0.02 M-sodium hydrogencarbonate aqueous solution, and the mixture reacted at 260° C. and 100 kPa for 20 minutes and at 270° C. and 100 kPa for 30 minutes. Thereafter, the degree of decompression was adjusted to 22 kPa, and the mixture reacted for 20 minutes. Then, the mixture reacted at the same temperature and the same pressure for 60 minutes. Next, the degree of decompression was adjusted to 16 kPa and the mixture reacted for 20 minutes, and the degree of decompression was further adjusted to 13 kPa and the mixture reacted for 20 minutes. Thereafter, when the degree of decompression was reduced to 130 Pa for 40 minutes and reached a predetermined torque through the reaction at the same pressure for 30 minutes, the vacuum was released with nitrogen gas to extract the polycarbonate resin.

The obtained polycarbonate resin had a weight average molecular weight (Mw) of 4250, and was a crystalline polymer having a Tg of 115° C. and a Tm of 172° C. (calorific value: 1.87 J/g).

A refractive index (n633) of this polycarbonate resin was 1.7708.

Example 14

A reactor equipped with a distiller was charged with 23.46 g (40 mmol) of 9,9-bis(2'-hydroxyethyl)-2,7-bis[dibenzo[b,d]furan-4"-yl]-9H-fluorene obtained in Example 3, 8.56 g (40 mmol) of DPC, and 15 µL (3×10$^{-6}$ mol) of a 0.02 M-sodium hydrogencarbonate aqueous solution, and the mixture reacted at 240° C. and 100 kPa for one hour. Thereafter, the degree of decompression was adjusted to 22 kPa and the mixture reacted for 20 minutes, and the degree of decompression was further adjusted to 13 kPa and the mixture reacted for 20 minutes. Thereafter, when the degree of decompression was reduced to 130 Pa for 40 minutes and reached a predetermined torque through the reaction at the same pressure for 30 minutes, vacuum was released with nitrogen gas to extract the polycarbonate resin.

A weight average molecular weight (Mw) of the obtained polycarbonate resin was 8430, and a Tg was 118° C.

A refractive index (n633) of this polycarbonate resin was 1.730.

Example 15

A polycarbonate resin was produced according to the operations in Example 14, except that in Example 14, 26.35 g (40 mmol) of 9,9-bis(2'-dihydroxyethyl)-2,7-bis[3-(naphthalen-2-yl-)phenyl]-9H-fluorene obtained in Example 5 was used instead of using 23.46 g (40 mmol) of 9,9-bis(2'-hydroxyethyl)-2,7-bis[dibenzo[b,d]furan-4"-yl]-9H-fluorene obtained in Example 3.

A weight average molecular weight (Mw) of the obtained polycarbonate resin was 5240, and a Tg was 105° C.

A refractive index (n633) of this polycarbonate resin was 1.735.

Example 16

A polycarbonate resin was produced according to the operations in Example 14, except that in Example 14, 24.27 g (40 mmol) of 9,9-bis(2'-dihydroxyethyl)-2,7-diphenanthren-9"-yl-9H-fluorene obtained in Example 6 was used instead of using 23.46 g (40 mmol) of 9,9-bis(2'-hydroxyethyl)-2,7-bis[dibenzo[b,d]furan-4"-yl]-9H-fluorene obtained in Example 3.

A weight average molecular weight (Mw) of the obtained polycarbonate resin was 5550, and a Tg was 126° C.

A refractive index (n633) of this polycarbonate resin was 1.718.

Example 17

A polycarbonate resin was produced according to the operations in Example 14, except that in Example 14, 23.63 g (40 mmol) of 9,9-bis(2'-dihydroxyethyl)-2,7-bis(4"-phenoxyphenyl)-9H-fluorene obtained in Example 8 was used instead of using 23.46 g (40 mmol) of 9,9-bis(2'-hydroxyethyl)-2,7-bis[dibenzo[b,d]furan-4"-yl]-9H-fluorene obtained in Example 3.

A weight average molecular weight (Mw) of the obtained polycarbonate resin was 4870, and a Tg was 67° C.

A refractive index (n633) of this polycarbonate resin was 1.715.

Example 18

A polycarbonate resin was produced according to the operations in Example 14, except that in Example 14, 26.35 g (40 mmol) of 9,9-bis(2'-dihydroxyethyl)-2,7-bis(4"-phenylnaphthalen-1"-yl)-9H-fluorene obtained in Example 9 was used instead of using 23.46 g (40 mmol) of 9,9-bis(2'-hydroxyethyl)-2,7-bis[dibenzo[b,d]furan-4"-yl]-9H-fluorene obtained in Example 3.

The obtained polycarbonate resin had a weight average molecular weight (Mw) of 6170, and was a crystalline polymer having a Tg of 122° C. and a Tm of 273° C. (calorific value: 8.82 J/g).

A refractive index (n633) of this polycarbonate resin was 1.796.

Example 19

A reactor equipped with a distiller was charged with 4.04 g (8 mmol) of 9,9-bis(2'-hydroxyethyl)-2,7-dinaphthalen-2"yl-9H-fluorene obtained in Example 2, 10.52 g (24 mmol) of 9,9-bis[4'-(2"-hydroxyethoxy)phenyl]-9H-fluorene, 1.32 g (8 mmol) of bisphenol A, 8.57 g (40 mmol) of DPC, and 15 µL (3×10$^{-6}$ mol) of a 0.02 M-sodium hydrogencarbonate aqueous solution, and the mixture reacted at 240° C. and 100 kPa for one hour. Thereafter, the degree of decompression was adjusted to 22 kPa and the mixture reacted for 20 minutes, and the degree of decompression was further adjusted to 13 kPa and the mixture reacted for 20 minutes. Thereafter, when the degree of decompression was reduced to 130 Pa for 40 minutes and reached a predetermined torque through the reaction at the same pressure for 30 minutes, vacuum was released with nitrogen gas to extract the polycarbonate resin.

A weight average molecular weight (Mw) of the obtained polycarbonate resin was 32500, and a Tg was 139° C.

A refractive index (n633) of this polycarbonate resin was 1.713.

In addition, the total transmittance of a sheet that is formed of the polycarbonate resin heat-pressed at 250° C. and has a thickness of 500 μm was 82%.

Example 20

A reactor equipped with a distiller was charged with 4.00 g (6 mmol) of 9,9-bis(2'-hydroxyethyl)-2,7-bis[4-(naphthalen-2-yl-)phenyl]-9H-fluorene obtained in Example 4, 7.98 g (18 mmol) of 9,9-bis[4'-(2"-hydroxyethoxy)phenyl]-9H-fluorene, 1.39 g (6 mmol) of bisphenol A, 6.55 g (30 mmol) of DPC, and 10 μL (2×10$^{-6}$ mol) of a 0.02 M-sodium hydrogencarbonate aqueous solution, and the mixture reacted at 270° C. and 100 kPa for one hour. Thereafter, the degree of decompression was adjusted to 22 kPa and the mixture reacted for 20 minutes, and the degree of decompression was further adjusted to 13 kPa and the mixture reacted for 20 minutes. Thereafter, when the degree of decompression was reduced to 130 Pa for 40 minutes and reached a predetermined torque through the reaction at the same pressure for 70 minutes, vacuum was released with nitrogen gas to extract the polycarbonate resin.

A weight average molecular weight (Mw) of the obtained polycarbonate resin was 27800, and a Tg was 157° C. The appearance of the polycarbonate resin was colorless and transparent.

Example 21

A reactor equipped with a distiller was charged with a mixture formed of 3.0375 g (6 mmol) of 9,9-bis(2'-hydroxyethyl)-2,7-dinaphthalen-2"yl-9H-fluorene obtained in Example 2, 6.1380 g (14 mmol) of 9,9-bis[4'-(2"-hydroxyethoxy)phenyl]-9H-fluorene, 4.8850 g (8 mmol) of 2,6-naphthalene dicarboxylic acid dimethyl ester, and 3.7 μl (50 ppm as Ti) of titanium tetraisopropoxide, and the mixture reacted at 280° C. and 100 kPa for one hour. Thereafter, the degree of decompression was adjusted to 20 kPa and the mixture reacted for 20 minutes, and the degree of decompression was further adjusted to 13 kPa and the mixture reacted for 20 minutes. Thereafter, when the degree of decompression was reduced to 130 Pa for 30 minutes and reached a predetermined torque through the reaction at the same pressure for 30 minutes, vacuum was released with nitrogen gas to extract the polyester resin.

A weight average molecular weight (Mw) of the obtained polyester resin was 6300, and a Tg was 118° C.

As described above, it can be understood that the polycarbonate resin obtained from the compound represented by General Formula (1) according to the present embodiment has a high refractive index.

The invention claimed is:

1. A compound represented by General Formula (1),

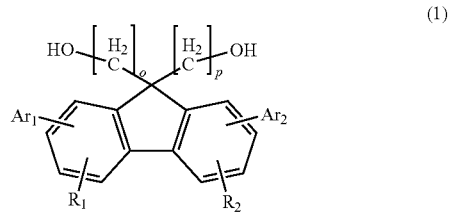

(1)

wherein in General Formula (1),
where, $R_1$ and $R_2$ each represent a hydrogen atom, a hydrocarbon group, or a heteroatom-containing hydrocarbon group,
$Ar_1$ and $Ar_2$ independently represent a group selected from the following formulae,

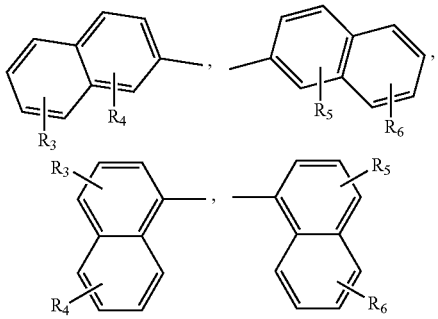

where, $R_3$ to $R_6$ each represent a hydrogen atom, a hydrocarbon group, or a heteroatom-containing hydrocarbon group,
o and p each represent an integer of 1 to 4.

2. The compound according to claim 1, wherein in General Formula (1), o and p each are 2.

3. A resin obtained by polymerization of the compound represented by General Formula (1) according to claim 1.

4. A polycarbonate resin derived from the compound represented by General Formula (1) according to claim 1.

5. An optical molded article containing the resin according to claim 3.

6. The optical molded article according to claim 5, wherein the optical molded article is an optical lens.

7. The optical molded article according to claim 5, wherein the optical molded article is an optical film.

8. An optical molded article containing the polycarbonate resin according to claim 4.

9. The optical molded article according to claim 6, wherein the optical molded article is an optical lens.

10. The optical molded article according to claim 6, wherein the optical molded article is an optical film.

* * * * *